United States Patent
Grassauer et al.

(10) Patent No.: US 11,510,859 B2
(45) Date of Patent: Nov. 29, 2022

(54) METHOD FOR IMPROVING AQUEOUS SOLUBILITY OF WATER-INSOLUBLE OR SLIGHTLY WATER-SOLUBLE DRUGS

(71) Applicant: MARINOMED BIOTECH AG, Vienna (AT)

(72) Inventors: Andreas Grassauer, Vienna (AT); Eva Prieschl-Grassauer, Vienna (AT); Angelika Bodenteich, Steyregg-Plesching (AT); Martina Morokutti-Kurz, Vienna (AT); Sabine Nakowitsch, Vienna (AT); Cornelia Kaintz, Vienna (AT)

(73) Assignee: MARINOMED BIOTECH AG, Korneuburg (AT)

( * ) Notice: Subject to any disclaimer, the term of this patent is extended or adjusted under 35 U.S.C. 154(b) by 637 days.

(21) Appl. No.: 15/767,290

(22) PCT Filed: Jul. 15, 2016

(86) PCT No.: PCT/EP2016/066999
§ 371 (c)(1),
(2) Date: Apr. 10, 2018

(87) PCT Pub. No.: WO2017/009480
PCT Pub. Date: Jan. 19, 2017

(65) Prior Publication Data
US 2019/0060202 A1 Feb. 28, 2019

Related U.S. Application Data

(63) Continuation-in-part of application No. 14/801,578, filed on Jul. 16, 2015, now abandoned.

(51) Int. Cl.
| | | |
|---|---|---|
| *A61K 8/60* | (2006.01) | |
| *A61K 9/107* | (2006.01) | |
| *A61K 47/26* | (2006.01) | |
| *A61K 47/18* | (2017.01) | |
| *A61K 8/42* | (2006.01) | |
| *A61K 47/10* | (2017.01) | |
| *A61K 47/46* | (2006.01) | |
| *A61K 8/9789* | (2017.01) | |
| *A61K 31/58* | (2006.01) | |
| *A61K 47/36* | (2006.01) | |
| *A61K 31/56* | (2006.01) | |
| *A61K 38/13* | (2006.01) | |
| *A61K 31/138* | (2006.01) | |
| *A61K 31/337* | (2006.01) | |

(Continued)

(52) U.S. Cl.
CPC ............ *A61K 8/604* (2013.01); *A61K 8/0291* (2013.01); *A61K 8/345* (2013.01); *A61K 8/42* (2013.01); *A61K 8/673* (2013.01); *A61K 8/9789* (2017.08); *A61K 9/006* (2013.01); *A61K 9/007* (2013.01); *A61K 9/0031* (2013.01); *A61K 9/0034* (2013.01); *A61K 9/0043* (2013.01); *A61K 9/0048* (2013.01); *A61K 9/1075* (2013.01); *A61K 31/12* (2013.01); *A61K 31/138* (2013.01); *A61K 31/337* (2013.01); *A61K 31/436* (2013.01); *A61K 31/56* (2013.01); *A61K 31/58* (2013.01); *A61K 38/13* (2013.01); *A61K 47/10* (2013.01); *A61K 47/18* (2013.01); *A61K 47/26* (2013.01); *A61K 47/36* (2013.01); *A61K 47/46* (2013.01); *A61Q 19/00* (2013.01); *A61K 2800/10* (2013.01); *A61Q 19/005* (2013.01)

(58) Field of Classification Search
CPC .................................................. A61K 2800/10
See application file for complete search history.

(56) References Cited

U.S. PATENT DOCUMENTS

| | | | |
|---|---|---|---|
| 4,868,170 A | | 9/1989 | Faustino et al. |
| 5,071,643 A | * | 12/1991 | Yu ........................ A61K 9/4858 |
| | | | 514/570 |

(Continued)

FOREIGN PATENT DOCUMENTS

| | | |
|---|---|---|
| CA | 1 119 957 A | 3/1982 |
| EP | 0 246 652 A2 | 11/1987 |

(Continued)

OTHER PUBLICATIONS

Walthelm et al. Effects of Saponins on the Water Solubility of Different Model Compounds. (Year: 2000).*

(Continued)

*Primary Examiner* — Sarah Alawadi
(74) *Attorney, Agent, or Firm* — Oliff PLC

(57) ABSTRACT

A method of increasing the solubility of a water-insoluble or slightly water-soluble hydrophobic organic compound in an aqueous solvent includes adding a saponin component selected from escin, glycyrrhizin, and *Quillaya saponaria* extract to the aqueous solvent in an amount sufficient to trigger the formation of micelles, wherein in a first step the hydrophobic organic compound is pre-dissolved in an organic solvent, and in a second step the organic solvent comprising the pre-dissolved compound is admixed to the aqueous solvent, whereby at least a part of the insoluble or slightly soluble hydrophobic organic compound gets solubilized and dissolved in the aqueous solvent, yielding an aqueous composition having an increased concentration of said organic compound dissolved therein. Also indicated are pharmaceutical or cosmetic compositions including a water-insoluble or slightly water-soluble organic compound dissolved in an aqueous solvent at substantially increased concentrations.

12 Claims, 11 Drawing Sheets

(51) Int. Cl.
  *A61K 8/02* (2006.01)
  *A61K 8/34* (2006.01)
  *A61K 31/436* (2006.01)
  *A61K 31/12* (2006.01)
  *A61K 9/00* (2006.01)
  *A61Q 19/00* (2006.01)
  *A61K 8/67* (2006.01)

(56) References Cited

U.S. PATENT DOCUMENTS

| | | | |
|---|---|---|---|
| 6,423,697 B1* | 7/2002 | Friedman | A61K 9/006 514/164 |
| 2006/0093560 A1* | 5/2006 | Chen | A61K 9/2866 424/48 |
| 2010/0034956 A1 | 2/2010 | Yasumi et al. | |

FOREIGN PATENT DOCUMENTS

| | | | |
|---|---|---|---|
| EP | 1094781 | * | 7/1999 |
| EP | 1 090 629 A1 | | 4/2001 |
| EP | 2 815 746 A1 | | 12/2014 |
| JP | 10-025255 | * | 1/1998 |
| WO | 02/074238 A2 | | 9/2002 |
| WO | 2006/029013 A2 | | 3/2006 |
| WO | 2014/163558 A1 | | 10/2014 |

OTHER PUBLICATIONS

Prasssas et al. Digitoxin Induced Cytotoxicity in Cancer Cells is Mediated through Distinct Kinase and Interferon Signaling Networks. (Year: 2011).*
Zillich et al. Polyphenols as Active Ingredients for Cosmetic Products. (Year: 2015).*
Aug. 25, 2016 Search Report issued in International Application No. PCT/EP2016/066999.
Aug. 25, 2016 Written Opinion of the International Seaching Authority issued in International Application No. PCT/EP2016/066999.

* cited by examiner

METHOD FOR IMPROVING AQUEOUS SOLUBILITY OF WATER-INSOLUBLE OR SLIGHTLY WATER-SOLUBLE DRUGS

FIELD

The present application is primarily in the field of organic chemistry and relates to a method of substantially increasing the solubility of water-insoluble or slightly water-soluble organic compounds, particularly of therapeutically or cosmetically useful drugs or agents, in aqueous solvents. The application further relates to aqueous pharmaceutical or cosmetic compositions comprising increased concentrations of dissolved water-insoluble or slightly soluble organic compounds of therapeutic or cosmetic value.

INTRODUCTION

In the majority of cases where an active pharmaceutical agent or drug needs to be systemically bioavailable, it should be readily soluble in mammalian body fluids. As these fluids are based on water, poor aqueous solubility of physiologically active organic compounds has always been and still is a challenging issue for drug developers.

Steroids constitute one prominent and important class of physiologically active and therapeutically important compounds, the aqueous solubility of which is so poor that they are classified among the lipids. Steroids are frequently reformul-ated into new drug preparations, which are primarily intended to treat hormonal imbalances or inflammatory conditions that may cause more or less severe pathological respiratory, dermatological, or ophthalmological symptoms. Drug developers have therefore sought suitable ways to improve delivery of low-solubility steroids to the skin, to mucosal tissues, or to the systemic circulation. As a result thereof, several practical solutions have been suggested and implemented.

Propylene glycol has been used as a solubilizer for various steroids of medical interest, especially for anti-inflammatory steroids. Canadian patent 1,119,957 discloses a solution of hydrocortisone in aqueous propylene glycol at slightly acidic pH, wherein the propylene glycol is provided at concentrations ranging from 15% to 50% by weight and the steroid is provided at concentrations of between 0.025% and 0.4% by weight of the composition.

Polyethylene glycol (PEG) has also been used together with propylene glycol to create solvents for steroids. European patent EP 246652 teaches flunisolide and beclomethasone in nasal spray formulations at concentrations of up to 0.05% weight per volume of the composition. U.S. Pat. No. 4,868,170 discloses lotions containing tipredane (a steroid having an aqueous solubility of less than 0.2 mg/l) at concentrations of up to 0.15% by weight, in a carrier system that contains PEG (molecular weight 350-500 Dalton) at 62-70% by weight plus propylene glycol at 10-20% by weight and water at 15-25% by weight. International patent application WO 2006/029013 claims combinations of propylene glycol (typically 2.5-15% wt) and propylene carbonate (typically 2.5-7.5% wt) to increase the steroid concentration in topical formulations of androstanes, in particular fluticasone propionate which is present in concentrations up to 0.1% by weight.

Dimethyl isosorbide has been found to enhance the solubility of prednisone, dexamethasone, and prednisolone when added to a solvent system comprising propylene glycol, polyethylene glycol, and water, with a maximum solubility of each drug being reached at or close to a dimethyl isosorbide/water or dimethyl isosorbide/propylene glycol concentration ratio of 1:2, implying that high concentrations of dimethyl isosorbide are required.

Most solvent systems for steroids including those mentioned above may be suitable for dermatological applications to the outer skin but do not sufficiently meet the requirements of oral or mucosal delivery of steroids in various therapeutic applications, and particularly so in the treatment of inflammatory conditions of the respiratory tract or the eyes. The reason being that the effective aqueous concentration of the steroid is far from optimal for the intended purpose, and/or the viscosity of the solution is too high to allow for a conven-ient application, e.g., for spraying very small droplets into the nose. Also, highly viscous compositions may create a sticky feeling in one's nose which is usually regarded as uncomfortable. Even worse, highly viscous eye drops may possibly interfere with sight. Also, the shear stress produced by vigorous mechanical agitation that is required to produce finely dispersed suspensions or emulsions in viscous solvent or carrier systems may be detrimental to high molecular weight compounds simultaneously present in the solvent or carrier systems as adjuvants or additives, such as, for example, carrageenans. And finally, many of these preparations usually encounter stability problems because steroids tend to precipitate after prolonged storage.

Generally, mucosal tissues are extremely sensitive and undesired side effects readily occur even with otherwise well tolerated compounds. For example, even the administration of pure water into the nose can cause sneezing and symptoms of a cold. Hence, there are limited options for developing aqueous formulations of water-insoluble compounds that would be suitable for mucosal administration.

Various antimalarial drugs come with an extremely limited aqueous solubility. For example artemisinin and its chemical derivatives are only slightly soluble in water. Lumefantrine, which is often used in combination with artemether, is practically insoluble (solubility 0.002%) in water. Curcumin, another potential antimalarial drug, is also afflicted with major weaknesses in terms of aqueous solubility, solution stability, and oral bioavailability.

Yet another class of compounds for which aqueous solubility is a limiting factor in many pharmaceutical preparations encompasses cyclic compounds having immunosuppressive and anti-inflammatory activity, such as cyclosporine A, which is a large cyclic peptoid; tacrolimus, also designated FK-506, which is a macrocyclic lactone; and sirolimus, another macrocyclic lactone, which is also known as rapamycin. These compounds have molecular weights even exceeding those of many steroids, and are structurally distinctly different from both steroids and common antimalarials. Many solutions of aqueous preparations have been described in the art that closely resemble those mentioned before. However, in all these cases the preparations are either complicated to manufacture, lack proper storage stability, and/or are not at least quasi-homogenous solutions.

It may therefore be inferred from the aforesaid that there still exists a need for augmenting the aqueous solubility of water-insoluble or slightly water-soluble therapeutically or cosmetically useful compounds in order to enable better topical or systemic bioavailability, as well as for improving physical and chemical storage stability.

BRIEF DESCRIPTION OF THE INVENTION

The inventors have surprisingly discovered that the poor solubility of many organic compounds in aqueous media can successfully be overcome and the solubility of such compounds amazingly increased severalfold and in many cases up to several orders of magnitude by the addition of a saponin component at very low concentrations to a said aqueous medium, typically a pharmaceutically or cosmetically acceptable aqueous solvent or solvent system, and admixing to the aqueous solvent or solvent system a portion of a desired water-insoluble or slightly water-soluble hydrophobic organic compound pre-dissolved in a conventional non-aqueous organic solvent.

Experiments conducted by the present inventors have proven that the solubilization effect of the saponins suitable for carrying out embodiments described herein is not limited to the interaction with a particular class of water-insoluble or slightly soluble compounds that share a close chemical, physiological or structural similarity but instead seems to be broadly applicable to a vast variety of hydrophobic organic compounds including the therapeutically useful compounds referred to herein.

Furthermore, the inventors have discovered that the addition of dexpanthenol can support and in some cases even improve the solubilizing effect of the saponins. Perhaps more importantly, it has been recognized that dexpanthenol is also able to stabilize the saponin-containing solutions during prolonged storage at ambient temperature.

Pharmaceutical or cosmetic compositions comprising a solvent system as described herein, whether with or without the addition of dexpanthenol as a solubilizer and/or stabilizer, are typically compatible with mucosal surfaces. When containing dexpanthenol they are stable at room temperature for at least one month, many of them even for at least 3 months, i.e., they do not disintegrate into multi-phase systems such as, e.g., liquid-liquid (fatty/aqueous) or liquid-solid (particulate/aqueous) phases and/or do not lose more than 5% of pharmaceutical or physiological activity during such a storage period. Typically, they are clear, transparent solutions that can be sterile filtered using conventional methods but may also be formulated into non-transparent preparations such as hydrocolloids, emulsions, suspensions, creams, gels or ointments, for specific applications.

Figure 1:
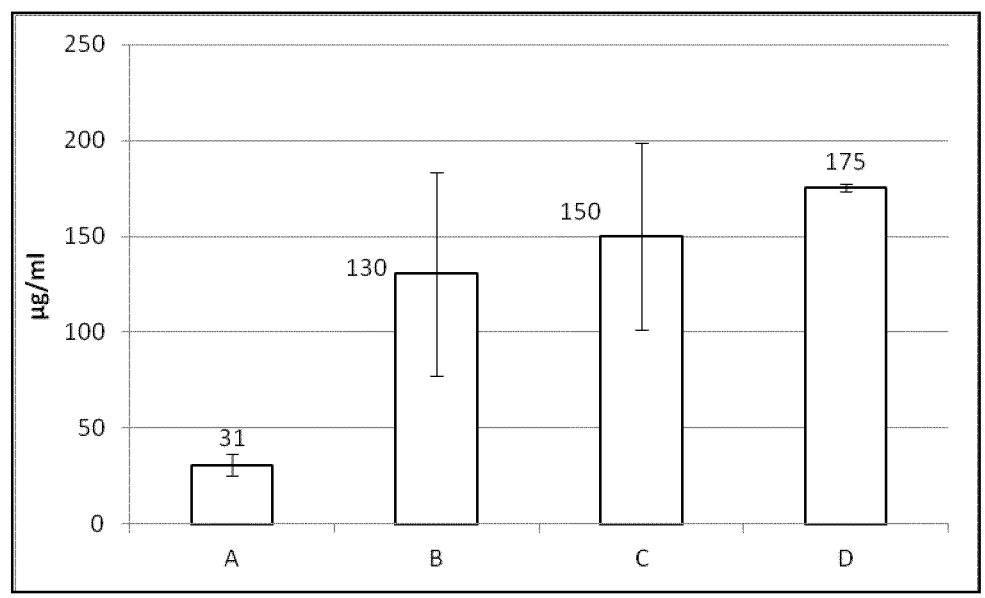
FIG. 1 represents the solubility of the glucocorticoid budesonide in 0.25× McIlvaine buffer (adjusted to pH 6.0) containing 0%, 5%, 10% and 15% (weight per volume) propylene glycol, without the addition of a saponin component and in the absence of dexpanthenol.

B=comparative budesonide suspension at 0.3 mg/ml;
C=experimental budesonide solution at 0.3 mg/ml.

DEFINITIONS

The term "steroid" as used herein shall mean any and all compound(s) that are based on the sterol core structure of four carbocycles, as depicted below in formula A.

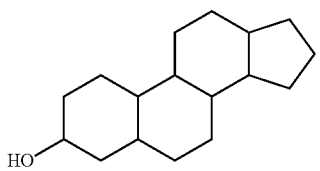

Formula A

Steroids exerting hormonal action are divided into two main classes: glucocorticoids, which control carbohydrate, fat and protein metabolism and frequently have anti-inflammatory action, and mineralocorticoids, which control electrolyte and water levels. The steroids referred to herein are typically cortico-steroids and may be selected from the group consisting of glucocorticoids and mineralocorticoids. Suitable examples comprise any one of budesonide, fluticasone, fluticasone propionate, and mometasone furoate.

The term "antimalarial" or "antimalarial drug" as used herein shall mean any and all compounds that are currently known or will be known in the future to terminate, reduce, or prevent infections with mosquito-transmitted intracellular para-sites of the genus *plasmodium*, and that are insoluble or only slightly soluble in water. Typical representatives of that category of compounds being artemisinins and lumefantrin.

The term "immunosuppressants" or "macrocyclic immunosuppressants" as used herein shall mean any and all macrocyclic molecules that are currently known or will be known in the future to reduce or suppress immune reactions in mammals, preferably those that bind immunophilins, and that are insoluble or only slightly soluble in water. Representative examples of such macrocyclic molecules include cyclosporin, tacrolimus, and sirolimus (rapamycin), and their chemical modifications, as well as compounds such as biolimus A9, zotaro-limus, everolimus, myolimus, novolimus, pimecrolimus, ridaforolimus, and temsirolimus.

The term "saponin" as used herein shall mean glycosides that comprise a triterpenoid or a steroidal aglycone core structure (the sapogenin) and one or more monosaccharide or oligosaccharide residues or chain(s) attached to the sapogenin. The saponins particularly preferred herein are escin, glycyrrhizin, and *Quillaja saponaria* extract.

The term "escin" as used herein shall encompass any and all saponins referred to in the literature under the terms alpha- and beta-escin, or alpha- and beta-aescin, respectively; their mixtures; their salts comprising mono-, di- or trivalent cations; and esters formed with organic acids and/or alcohols, particularly with low molecular weight, organic acids and/or alcohols, primarily monovalent acids and/or alcohols.

The term "glycyrrhizin" as used herein shall be understood as being equivalent to the term glycyrrhicinic acid in both its 18-alpha and 18-beta forms.

The term *Quillaja saponaria* extract as used herein shall refer to the commercially available product *Quillaja Saponaria* (Soapbark Extract) which is approved as an ingredient for use in food and beverages (GRAS) by the United States FDA under Title 21 CFR 172-510, FEMA number 2973. It is also approved as an ingredient for analogous use in the European Union under code E 999, Current CAS number: 068990-67-0 or EPA List 4A CAS number: 1393-03-9 (*Quillaja Saponin*).

The term "inflammatory condition" as used herein shall encompass all acute or chronic conditions where mammalian body tissue is affected by at least one symptom selected from the group consisting of edema, swelling, locally elevated temperature, tenderness, and pain, and/or by elevated levels of inflammation markers such as reactive protein C, or pro-inflammatory cytokines, or by any combination of such symptoms and elevated levels of inflammation markers.

The term "anti-inflammatory steroid" shall encompass all steroids that are able to reduce any of the above symptoms of inflammation in a mammalian body. The most important members of this group are the glucocorticoids.

DETAILED DESCRIPTION

It has been recognized by the present inventors that even small amounts of saponins, when added to an aqueous solvent, are capable of dramatically increasing the aqueous solubility of hydrophobic organic compounds including numerous therapeutically relevant compounds. The concentrations of effectively dissolved hydrophobic organic compound material in aqueous solvents obtainable in accordance with the invention are at least several times and up to several orders of magnitude higher than the concentrations of the same compounds in conventional saponin-free aqueous, e.g. water/propylene glycol, solvent systems.

The experimental data produced so far suggest that the saponin component in the concentrations required for the improvement of solubilization forms specific micelles or micelle-like structures with the hydrophobic organic compounds and in doing so reduces the contact area of the hydrophobic parts of such compounds with the aqueous environment, hence reduces hydrophobicity and increases water-solubility.

Apart from the saponin effect, adding dexpanthenol to compositions prepared in accordance with the invention at concentrations usually higher than those of the saponins and in some embodiments at concentrations within a range of from 1 to 5% v/v, may prevent precipitation of the dissolved hydrophobic organic compounds, especially of steroids, during storage. It may further prevent the disintegration of the mixture of ingredients of such compositions into multi-phase system during long-term storage at room temperature. Moreover, the present invention allows for adjusting the concentrations of the saponins and of dexpanthenol to fully meet the requirements for application to the sensitive mucosal surfaces of the nose, the mouth, of the eyes, of the respiratory tract, of the intestinal tract, of the genital and anorectal regions, and of other parts of the mammalian body.

Accordingly, in an embodiment the invention relates to a method of improving storage stability of aqueous solutions of solubilized water-insoluble or only slightly water-soluble hydrophobic organic compounds, wherein in addition to the saponin component, dexpanthenol is added as a solubilization enhancer and/or as a stabilizing agent.

It shall be pointed out at this occasion that the principle of the present invention may also be applied to existing water-containing solutions, suspensions, emulsions or hydrocolloids of such water-insoluble or slightly soluble compounds, in particular of therapeutically or cosmetically applied compounds, by adding either or both of a saponin component and a dexpanthenol component to such a solution, suspension, emulsion or hydrocolloid. The result being a substantial increase in the concentration of effectively dissolved hydrophobic compound material, i.e. of previously undissolved hydrophobic compound material converted into a dissolved state.

This will have in effect that the bioavailability of these compounds will be enhanced as well, thereby improving the pharmacokinetics and reaction dynamics of the hydrophobic compounds in the recipient's body, and will also trigger an earlier onset of the desired pharmacological action in case of pharmaceutically active compounds.

In addition, it shall be emphasized that particle-free and usually clear and transparent solutions prepared in accordance with a method of the present invention are susceptible to direct sterile filtration. This is in contrast to state-of-the-art methods for obtaining sterile filtered two-phase preparations, i.e. suspensions, emulsions or hydrocolloids, which methods typically comprise sterile filtering a purely organic solution comprising the desired hydrophobic compound, and, independently, sterile filtering an aqueous buffer, and mixing the aqueous buffer with the organic solution. However, this procedure causes the majority of the hydrophobic compound molecules dissolved in the organic phase to precipitate upon contact with the aqueous buffer, thus resulting in a suspension, emulsion or a hydrocolloid containing only a very low amount of effectively solubilized compound together with a much bigger amount of undissolved, optionally particulate, matter of said compound.

Such methods of producing sterile preparations can also be used in embodiments of the present invention, the difference being, however, that the aqueous buffer component further comprises a saponin and optionally also dexpanthenol, resulting in preparations similar to those known in the art, wherein the concentration of dissolved hydrophobic compound is, however, substantially increased relative to the corresponding preparations known in the art without the saponin and the optional dexpanthenol components.

Accordingly, an embodiment herein relates to aqueous two-phase preparations, i.e. preparations selected from the group consisting of suspensions, emulsions, and hydrocolloids, comprising a saponin and optionally also a dexpanthenol component, wherein the concentration of effectively dissolved hydrophobic organic compound is substantially increased over the one achieved in a corresponding conventional preparation without the saponin and the optional dexpanthenol component.

Given that many state-of-the-art preparations comprising hydrophobic compounds are based on solvent systems comprising one or more organic solvents together with a suitable amount of water, it is also an object herein to provide a method for reducing the share of the non-aqueous organic solvent or solvent mixture in a composition comprising a slightly water-soluble or water-insoluble hydrophobic organic compound, and to simultaneously increase the share of the purely aqueous solvent or buffer system in that composition. This will overcome various drawbacks of state-of-the-art preparations as discussed in more detail above and will allow for largely expanding the scope of therapeutic or cosmetic applications, and particularly with regard to prophylactic or therapeutic oral as well as parenteral, e.g., transdermal and transmucosal, applications of such hydrophobic organic compounds or drugs.

Accordingly, another embodiment herein relates to a water-based solvent system for insoluble or slightly water-soluble compounds comprising an aqueous solution and one or more saponins, and optionally dexpanthenol, in addition to conventional organic solvents or solubilizers used in the art for dissolving such compounds.

The term "improving the solubility of hydrophobic compounds" as used herein shall be understood as to render hydrophobic compounds better water-soluble without chemical modification of the compounds. More specifically, this encompasses significantly increasing the concentration an insoluble or sparingly water-soluble compound in its dissolved, non-particulate state in an aqueous solvent relative to the compound's concentration in the dissolved state that could have been achieved without applying the principle of the present invention.

The term "improving the stability" of an aqueous solution of hydrophobic compounds as indicated herein shall be understood as to significantly increase the storage stability of an aqueous solution of a hydrophobic compound relative to the storage stability that could have been achieved without the addition of dexpanthenol. More specifically, "storage stability" shall be understood as a pharmaceutical or cosmetic composition's capability of remaining substantially unchanged over a predetermined period of time, i.e., without the occurrence of any signs of precipitation of the dissolved compound(s) of interest, without any signs of disintegration of the composition into two or more phases such as liquid-liquid phases (emulsion) or liquid-solid phases (suspension), and preferably without a significant loss in physiological activity of the composition.

The various classes or categories of chemically diverse and physiologically distinctly different pharmaceutically active agents referred to herein have in common that they are highly hydrophobic in nature hence only slightly, if at all, water-soluble. Accordingly, while the hydrophobic compounds explicitly referred to herein are suitable examples for use in accordance with the present invention, it will be apparent to those of ordinary skill in the art that the invention may be applied to any such classes or categories of hydrophobic and sparingly water-soluble chemical compounds, whether or not physiologically active or cosmetically useful. Thus, the examples of water-insoluble or slightly soluble hydrophobic organic compounds explicitly referred to herein as being eligible for improvement in aqueous solubility are not exhaustive and shall therefore not be construed as limiting the scope of the present invention laid down in the claims.

One representative of the saponin component most useful herein is escin. Escin is a well-known triterpene saponin product that can be obtained from horse chestnuts (the fruits of *Aesculus hippocastanum*) by extraction with alcohol and other organic solvents. It is a mixture of closely related highly hydroxylated triterpene derivatives in which tiglic acid or acetic acid are bound as esters while two glucuronic acid molecules are attached through glycosidic bonds. The components in the mixture constituting escin differ with respect to their sugar residues, and also with respect to the acetyl substituent of the aglycone. The main glycoside in escin has the following chemical structure (formula B):

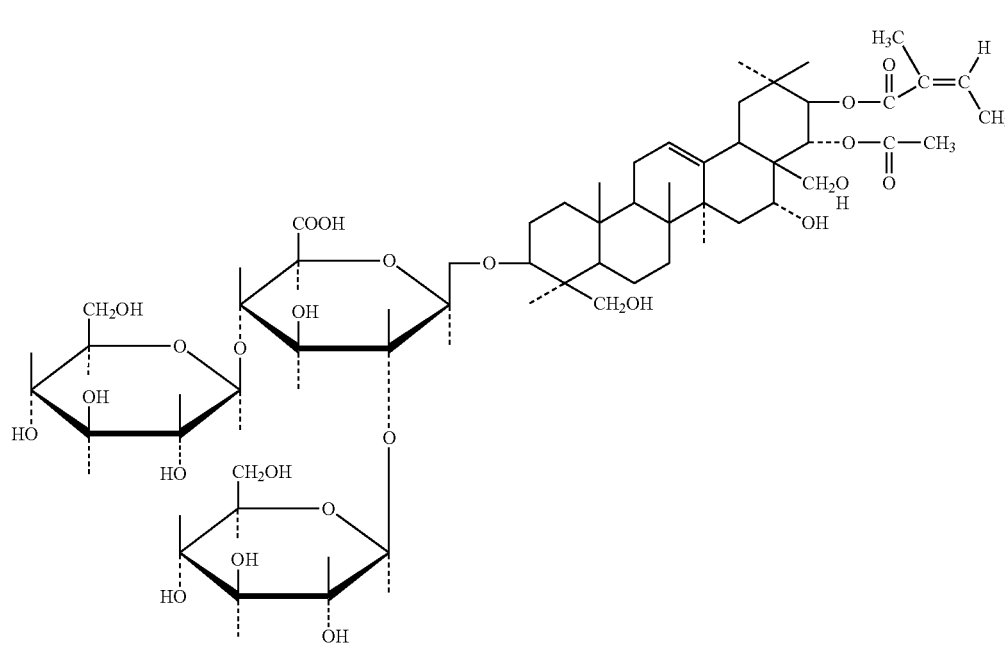

Formula B

Escin-based formulations have been used for treating various conditions of venous insufficiency and excessive microvascular permeability for several decades. Topical gels containing escin are commercially available for the treatment of local edema from varicose veins or hemorrhoids which typically contain propylene glycol, isopropanol, and carbomers. Oral escin preparations are also available.

European Patent EP 1 090 629 teaches combinations of escin and dextran sulfate to prevent or treat irritations around an individual's eye.

Glycyrrhizin, a saponin from *Glycyrrhiza glabra*, consists of the triterpene glycyrrhetinic acid aglycone and glucuronic acid. It is the sweet-tasting component of licorice, and has many uses in the food and cosmetics industry. Glycyrrhizin has reportedly anti-inflammatory, anti-diabetic, antioxidant, anti-tumor, antimicrobial, anti-viral, and hepatoprotective properties. Its structure is as follows (formula C):

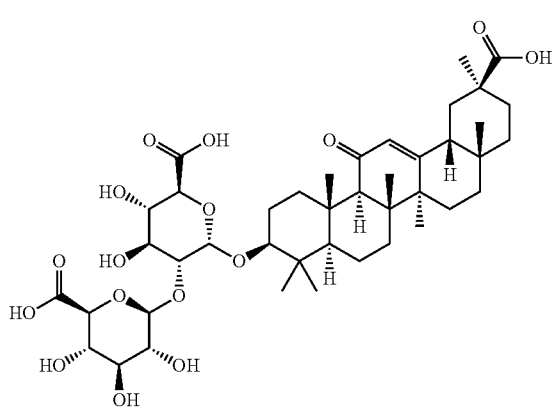

Formula C

International patent application WO2002/074238 discloses the use of glycyrrhizin in the preparation of highly water-soluble complexes of a broad variety of sparingly soluble compounds that contain at least one nitrogen atom. The complexes are preferably ionic and the molar ratio of glycyrrhizin to active agent is preferably 1:1 to 1:3.

In contrast, the embodiments of the present invention require no nitrogen atom in the compounds to be solubilized, require no ionic states to be present, and require only low amounts of saponins, i.e., amounts that are far below the ones taught in WO2002/074238 for glycyrrhizin and that are typically in a range of only fractions of the amounts of the compounds to be solubilized. Nevertheless, glycyrrhizin may be applied in accordance with the invention either as a free base or in form of its salts, particularly its potassium or ammonium salts, and optionally in combination with another saponin, following the protocol described herein. Surprisingly, its aglycone, i.e. glycyrrhetinic acid or enoxolone, may not be used as a solubilization enhancer in accordance with the invention.

The saponin component as used herein is typically provided at concentrations ranging from 0.01% to 10% weight by volume (w/v) of the final cosmetic or pharmaceutical preparation containing the desired water-insoluble or slightly soluble organic compound. In various embodiments, the concentration of the saponin component will be in a range of from 0.02% to 0.1% or from 0.5 to 5% weight by volume of the final aqueous solution or preparation, respectively, depending on the kind of saponin used in a given embodiment for a specific purpose.

Dexpanthenol, the D-enantiomer (or stereochemically, the R-form) of panthenol, is the amide of pantoic acid and β-alanine. Because it is an essential nutrient required to synthesize coenzyme A, it is also known as vitamin B5. Its structure is as follows (formula D):

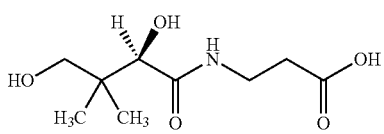

Formula D

Dexpanthenol is widely used as an emollient and humectant in cosmetics and topical personal care products and it also has medical utility. More specifically, it may support the healing of small dermal abrasions, local first-degree burns, and dermatoses.

It has been found that dexpanthenol could be useful as a stabilizer for solutions of insoluble or sparingly water-soluble compounds prepared either according to methods known in the art or according to the present application.

The dexpanthenol component as used herein is typically provided at concentrations ranging from 0.5% to 10% volume by volume (v/v) of the final preparation, e.g. a cosmetic or pharmaceutical composition containing the desired water-insoluble or slightly soluble organic compound. In various embodiments, the concentration of the dexpanthenol component will be in a range of from 1% to 5% volume by volume of the final solution or composition.

Various pharmaceutical compositions comprising as a physiologically active ingredient a sparingly water-soluble organic compound are currently being used in the treatment of inflammatory conditions, in the treatment of diseases such as malaria, and also in the treatment of autoimmune disorders and in the course of post-operative immunosuppression in connection with graft surgery. For example, cyclophilin-binding immunosuppressive drugs are currently being used to treat autoimmune disorders that cause conditions such as atopic dermatitis, psoriasis, vitiligo, ulcerative colitis, rheumatoid arthritis, systemic lupus, and autoimmune uveitis. Specific immunosuppressants from this group may also be administered in order to prevent undesired immune reactions such as a rejection of an allogeneic organ transplant, including graft-versus-host disease from bone marrow transplants. All of these compositions may be substantially improved in accordance with embodiments of the invention described herein.

The aqueous solutions prepared in accordance with the invention typically comprise one or more pharmaceutically or cosmetically acceptable non-aqueous solvents, carriers, and/or excipients, and optionally further comprise preservatives and/or other additives. The solvents, carriers and/or excipients may be selected from the group comprising polyethylene glycols such as PEG-400; fatty acid alcohols such as stearyl, cetyl, or oleyl alcohol, triacetin monostearate, ethylene glycol distearate, glyceryl monostearate, propylene glycol monostearate, and polyvinyl alcohol; carbomers such as carboxy polymethylene; DMSO; non-ionic polyethoxylated detergents obtained by reacting hydrogenated castor oil with ethylene oxide such as those known under the brand name Cremophor®; and chemically modified cellulose derivatives such as carboxy-methylcellulose, and hydroxypropyl cellulose.

The other additives may comprise detergents, emulsifiers and/or surfactants optionally selected from the group comprising sorbitan fatty acid esters such as polyoxyethylene sorbitan and its monolaurate and monooleates (e.g., Tween 20, Tween 60, or Tween 80), sorbitan palmitate, oleate, and stearates (e.g., Span 40, Span 60, Span 65, or Span 80); polyoxyethylene esters; polyethylene glycol fatty acid esters such as Cremophor™; diethylene glycol monolaurate, triethanolamine oleate, ethyl laurate, sodium lauryl sulfate, Pluronic F68, Poloxamer 188; and the preservatives may be selected from the group comprising cetrimonium bromide, cetylpyridinium chloride, benzalkonium chloride, and/or mixtures of the foregoing compounds.

The pharmaceutical compositions of embodiments described herein may be adjusted for various modes of administration. For example, they may be adjusted for systemic absorption using one of the oral, parenteral, or transmucosal routes; or they may be adjusted for topical use on dermal or mucosal tissues.

Compositions for parenteral use may be specifically adapted for intravascular infusion or for bolus injection.

Oral drug compositions intended for swallowing may be formulated as sweet syrups but may also be formulated into soft or hard capsules or other suitable galenic forms.

Compositions for mucosal and transmucosal administration will typically be formulated as gels, creams, ointments, sprays, mouthwashes, gargling solutions, solutions for inhalation, or suppositories, as the case may be.

The compositions described herein may also contain carrageenans. The carrageenans most frequently used are iota-, kappa- and lambda-carrageenan, wherein iota- and kappa-carrageenans have specific antiviral and antiallergic activities.

The following examples are for illustrative purposes and shall facilitate understanding of the invention without confining the invention to the examples explicitly disclosed hereinafter.

Example 1: Nasal Spray with Budesonide (5% Final Propylene Glycol Concentration)

Preparation of Solutions
A. Budesonide Pre-Solution
1 g budesonide was weighed in a glass flask, dissolved under gentle stirring and heating in propylene glycol, and filled up to 100 ml with propylene glycol. The concentration of actually dissolved budesonide measured by HPLC was 10 mg/ml.
B. McIlvaine Buffer
The following substances were weighed and dissolved in distilled water to produce 1× McIlvaine Buffer pH 6: 22.52 g $Na_2HPO_4 \times 2H_2O$, 7.73 g citric acid monohydrate, 4.0 g EDTA sodium. Distilled water was added to give 1000 ml solution of pH 6, which was sterile filtered and stored at room temperature.
C. Escin Containing McIlvaine Buffer
0.5 g escin was weighed and dissolved in 1× McIlvaine buffer, filled up to 250 ml and sterile filtered (hereinafter named McIlvaine 0.05%, because this solution was used to prepare samples containing a final concentration of 0.05% escin). Other escin concentrations in McIlvaine buffer were prepared by mixing different parts of McIlvaine buffer and McIlvaine 0.05% as described in Table 1.

TABLE 1

Preparation of buffers with different Escin concentrations

| Buffer Name | McIlvaine 0.05% [ml] | McIlvaine buffer [ml] |
|---|---|---|
| McIlvaine 0.03% | 30 | 20 |
| McIlvaine 0.02% | 20 | 30 |
| McIlvaine 0.01% | 10 | 40 |

D. Carrageenan Stock Solution a) 2.4 g iota-carrageenan was weighed and dissolved in distilled water under mild heating and stirring and filled up to 1000 ml with distilled water.

b) 2.4 g iota-carrageenan and 0.8 mg/ml kappa-carrageenan were weighed and dissolved in distilled water under light heating and stirring and filled up to 1000 ml with distilled water.

Solutions were put for 1 h at 80° C. followed by hot sterile filtration.

Commercially available carrageenan products are frequently mixtures of iota-, kappa- and/or lambda carrageenan. For most embodiments referred to herein the carrageenan component used for the manufacture of the various preparations shall be understood as comprising at least 50% wt, usually at least 80% wt, and typically at least 90% by weight of either iota carrageenan or of a combination of iota- and kappa-carrageenan, relative to the total of all carrageenans present in the carrageenan product used herein.

E. Preparation of Experimental Compositions

Samples of series A (0% dexpanthenol): 2.5 ml solution containing the respective escin concentration (McIlvaine 0.01%, 0.02%, 0.03% or McIlvaine buffer) were mixed with 5 ml carrageenan stock solution and 0.5 ml budesonide pre-solution and filled up to 10 ml with distilled water.

Samples of series B (2% dexpanthenol): 2.5 ml solution containing the respective escin concentration (McIlvaine 0.01%, 0.02%, 0.03% or McIlvaine buffer) were mixed with 0.2 ml dexpanthenol, 5 ml carrageenan stock solution and 0.5 ml budesonide pre-solution and filled up to 10 ml with distilled water. Samples of series C (5% dexpanthenol): 2.5 ml solution containing the respective escin concentration (McIlvaine 0.01%, 0.02%, 0.03% or McIlvaine buffer) were mixed with 0.5 ml dexpanthenol, 5 ml carrageenan stock solution and 0.5 ml budesonide pre-solution and filled up to 10 ml with distilled water. The resulting formulations were put at 80° C. for 1 h before hot sterile filtration. The samples were filled in glass vials and stored for 3 months at room temperature.

Analysis of Experimental Compositions

After 3 months storage at room temperature, samples were taken and centrifuged for 11 min at 15700 rcf. The clear supernatant was filled into glass vials and the concentration of dissolved budesonide (maximal 500 μg/ml) was measured in duplicates by HPLC.

HPLC Method:

Budesonide was analyzed by RP-HPLC (UV absorbance detection at 244 nm) using isocratic elution with 55% acetonitrile 0.01% TFA/45% water 0.01% TFA at 1 ml/min for 7 min on an Agilent Zorbax SB C18 3.5 μm 4.6×150 mm column with 4×4 mm RP8 pre-column. From the budesonide-containing samples 40 μl were injected and analyzed.

The system was calibrated with ten dilutions in the range of 20 to 640 ng/μl budesonide in acetonitrile/water 2:8. From the calibration samples 25 μl each were injected in triplicates, spanning a range of 0.5 to 16 μg budesonide per analysis.

Figure 8A:
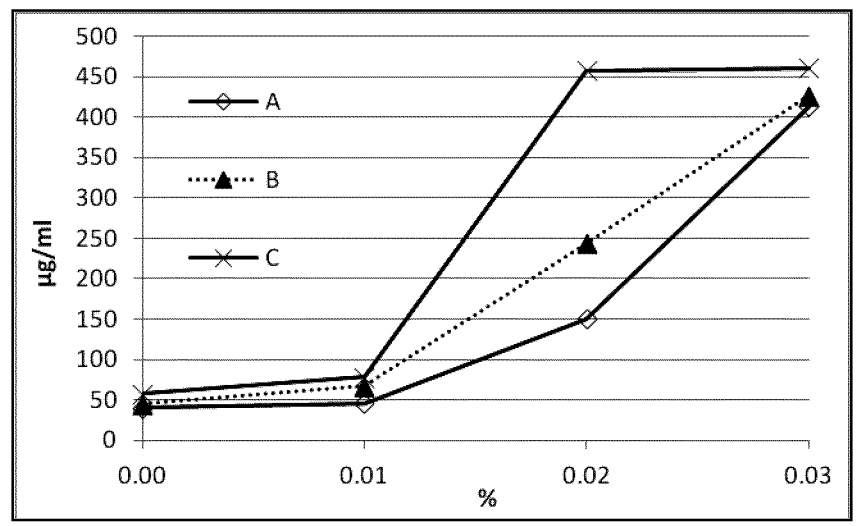
FIG. 8a represents the relationship between dissolved budesonide (y-axis) in McIlvaine buffer containing 5% propylene glycol and 1.2 g/L iota-carrageenan, and varying dexpanthenol and escin concentrations after 3 months of storage at ambient temperature (T≈20-25° C.): dexpanthenol concentrations at 0% (series A), 2% (series B), or 5% v/v (series C); x-axis=escin concentrations.
Figure 8B:
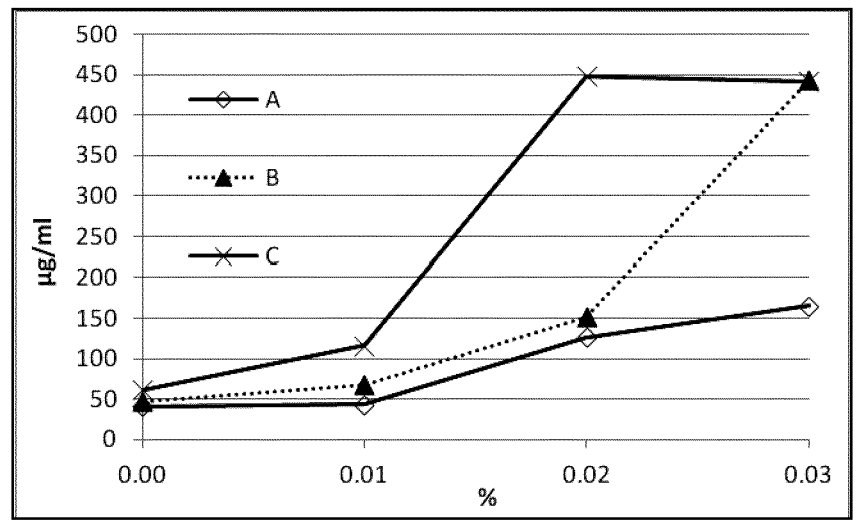
FIG. 8b represents analogous data obtained from an identical experimental set up as in FIG. 8a except for the fact that the experimental solution further contained 0.4 g/L kappa-carrageenan.

The results obtained from the solubility enhancement experiments are described below and are depicted in FIGS. 8a and 8b. The experimental solutions disclosed in Example 1 can be adjusted as pharmaceutical compositions for topical use, particularly for percutaneous or transmucosal administration. In an embodiment, the solutions are adapted as nasal sprays.

It is preferred herein that nasal sprays contain no more than 0.05% w/v escin in order to avoid undesired side effects in the sensitive nasal mucosa. In order to optimize the solubility enhancing activity of the saponin component, glycyrrhizin and/or *Quillaja saponaria* extract may be supplemented to escin at acceptable concentrations set out hereinafter.

The carrageenans optionally present in the compositions along with the anti-inflammatory steroid may contribute as antiallergic and/or antiviral active adjuvants to the overall therapeutic efficacy of the compositions.

Example 2: Nasal Spray with Budesonide (10% Final Propylene Glycol Concentration)

Preparation of Solutions

Solutions were prepared as described in Example 1, paragraphs A-D

Preparation of Experimental Compositions

Samples of series A (0% dexpanthenol): 2.5 ml solution containing the respective escin concentration (McIlvaine 0.01%, 0.02%, 0.03% or McIlvaine buffer) were mixed with 5 ml carrageenan stock solution, 0.5 ml propylene glycol and 0.5 ml budesonide pre-solution and filled up to 10 ml with distilled water.

Samples of series B (2% dexpanthenol): 2.5 ml solution containing the respective escin concentration (McIlvaine 0.01%, 0.02%, 0.03% or McIlvaine buffer) were mixed with 0.2 ml dexpanthenol, 5 ml carrageenan stock solution, 0.5 ml propylene glycol and 0.5 ml budesonide pre-solution and filled up to 10 ml with distilled water.

Samples of series C (5% dexpanthenol): 2.5 ml solution containing the respective escin concentration (McIlvaine 0.01%, 0.02%, 0.03% or McIlvaine buffer) were mixed with 0.5 ml dexpanthenol, 5 ml carrageenan stock solution, 0.5 ml propylene glycol and 0.5 ml budesonide pre-solution and filled up to 10 ml with distilled water.

The resulting formulations were heated up to and maintained at 80° C. for 1 h before hot sterile filtration. The samples were filled in glass vials and stored for 1 month at room temperature.

Analysis of Experimental Compositions

After 1 month storage at room temperature, samples were taken and centrifuged for 11 min at 15700 rcf. The clear supernatant was filled into HPLC analysis glass vials and the concentration of dissolved budesonide (maximum 500 μg/ml) was measured in duplicates by HPLC. HPLC method as described in Example 1

Figure 9A:
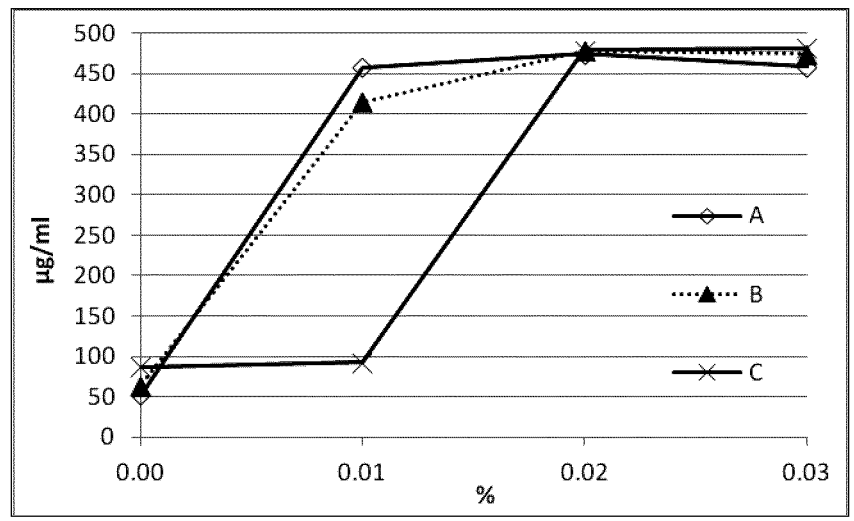
FIG. 9a represents the relationship between the concentrations of dissolved budesonide (y-axis) in McIlvaine buffer containing 10% propylene glycol, 1.2 g/L iota-carrageenan, and optionally dexpanthenol on one hand, and the saponin concentration on the other hand after one month of storage at ambient temperature; x-axis=escin concentration.
Figure 9B:
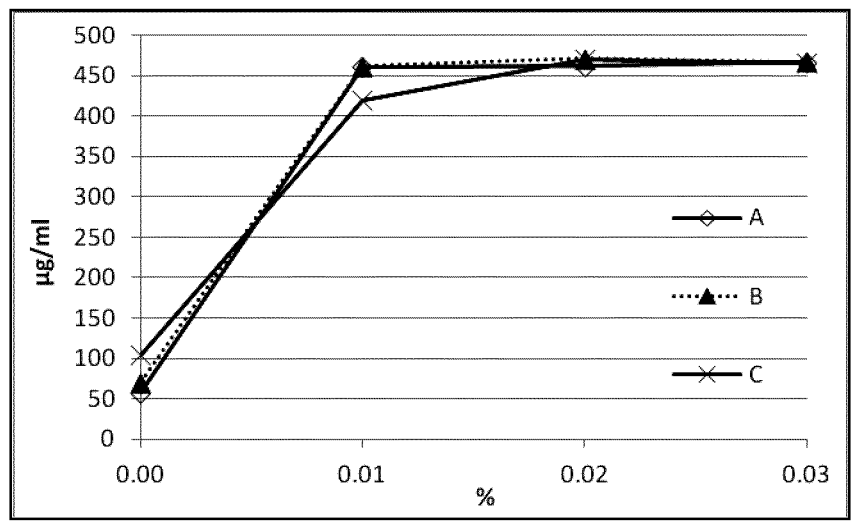
FIG. 9b represents analogous data obtained from an identical experimental set up as in FIG. 9a except for the fact that the experimental solution further contained 0.4 g/L kappa-carrageenan.

The results obtained from the solubility enhancement experiments are described below and are depicted in FIGS. 9a and 9b. The experimental solutions disclosed in Example 2 can be adjusted as pharmaceutical compositions for topical use, particularly for percutaneous or transmucosal administration. In an embodiment, the solutions can be adapted as nasal sprays.

Example 3: Eye Drop Formulation with Fluticasone Propionate

Preparation of Solutions

A. Fluticasone Propionate Pre-Solution 1 mg fluticasone propionate was weighed in a glass flask and dissolved in propylene glycol and filled up to 10 ml with propylene glycol. The concentration of fluticasone propionate determined by HPLC was 100 μg/ml.

B. McIlvaine Buffer

As described in Example 1

C. McIlvaine Buffer Containing Escin

As described in Example 1

D. Hyaluronic Acid Stock Solution 2.5 g hyaluronic acid were weighed and dissolved in distilled water under mild heating, filled up to 120 ml with distilled water, and held at 80° C. for one hour before hot sterile filtration.

Preparation of Experimental Compositions

Samples of series A (0% dexpanthenol): 2.5 ml solution containing the respective escin concentration (McIlvaine 0.01%, 0.02%, 0.03% or McIlvaine buffer) were mixed with 3.6 ml hyaluronic acid stock solution and 0.5 ml Fluticasone propionate pre-solution and filled up to 10 ml with distilled water. Samples of series B (2% dexpanthenol): 2.5 ml solution containing the respective escin concentration (McIlvaine 0.01%, 0.02%, 0.03% or McIlvaine buffer) were mixed with 0.2 ml dexpanthenol, 3.6 ml Hyaluronic acid stock solution and 0.5 ml fluticasone propionate pre-solution and filled up to 10 ml with distilled water.

Samples of series C (5% dexpanthenol): 2.5 ml solution containing the respective escin concentration (McIlvaine 0.01%, 0.02%, 0.03% or McIlvaine buffer) were mixed with 0.5 ml dexpanthenol, 3.6 ml hyaluronic acid stock solution and 0.5 ml fluticasone propionate pre-solution and filled up to 10 ml with AD.

The resulting formulations were put at 80° C. for 1 h before hot sterile filtration. The samples were filled in glass vials and stored for 1 month at room temperature.

Analysis of Experimental Compositions

After 1 month storage at room temperature, samples were taken and centrifuged for 11 min at 15700 rcf. The clear supernatant was filled into glass vials and the concentration of dissolved FP (maximal 5 µg/ml) was measured in duplicates by HPLC.

HPLC Method:

Fluticasone propionate in the presence of hyaluronic acid was analyzed by RP-HPLC (UV absorbance detection at 235 nm) using a gradient from 5% acetonitrile to 90% acetonitrile in water containing 0.01% TFA (see detailed gradient description below).

Solvent A: water HPLC gradient grade 0.01% trifluoroacetic acid. Solvent B: acetonitrile HPLC gradient grade 0.01% trifluoroacetic acid, flow 1 ml/min. A gradient of 5-90% solvent B for 10 min, 90% solvent B for 2 min, 90-5% solvent B for 2 min and 5% solvent B for 1 min was run on a HPLC column Thermo Aquastar 4.6×150 mm, S/N 0202797K with a 4×4 RP-8 Merck pre-column at 25° C. From the fluticasone propionate containing samples 40 µl each were injected and analyzed. Fluticasone propionate eluted as symmetric peak at about 9.95 min.

The system was calibrated with seven dilutions in the range of 0.1 to 80 ng/µl fluticasone propionate in acetonitrile/water 4:6 containing a range from 0.5 to 2000 ng per analysis.

Figure 10:
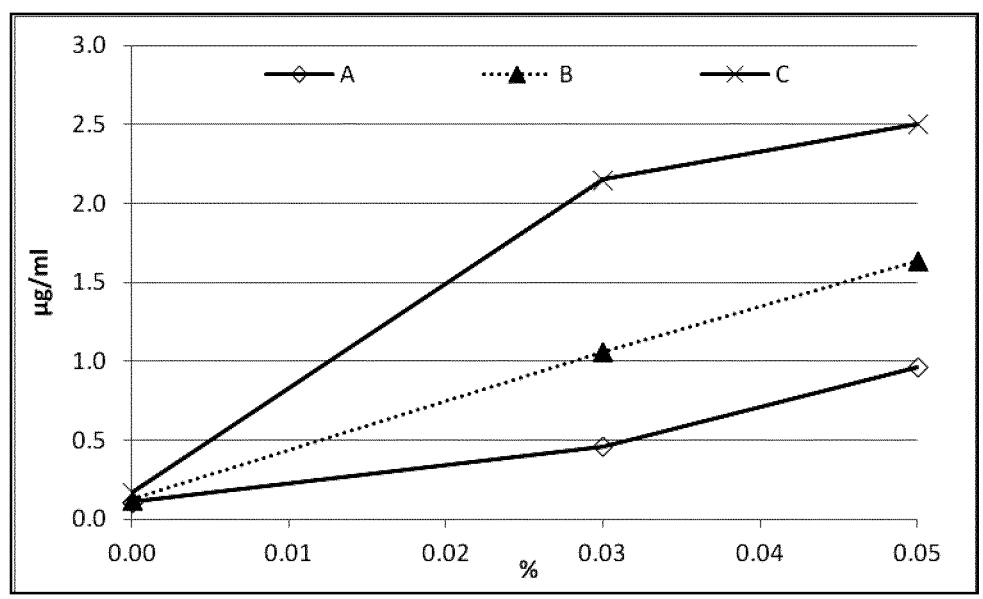
FIG. 10 represents the concentrations of dissolved fluticasone propionate (y-axis) in McIlvaine buffer containing 5% propylene glycol, 7.5 g/l hyaluronic acid, and optionally dexpanthenol, in relation to varying escin concentrations (x-axis) after one month of storage at ambient temperature; A . . . 0% Dexpanthenol; B . . . 2% Dexpanthenol; C . . . 5% Dexpanthenol; x-axis . . . w/v % Escin; y-axis . . . µg/ml Fluticasone propionate.
Figure 11A:
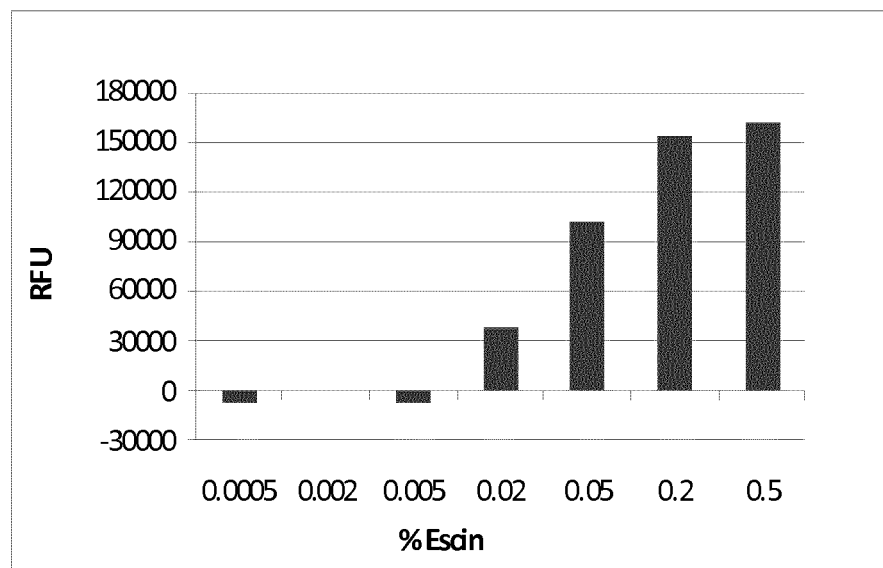
FIGS. 11a and 11b represent the relationship of the concentrations of either escin (FIG. 11a) or glycyrrhizin (FIG. 11b) on the formation of micelles, as determined by using a fluorescent dye (Hoechst 33342) in water at room temperature as a suitable indicator; x-axis=% escin or % glycyrrhizin; y-axis=relative fluorescent units (RFU).
Figure 11B:
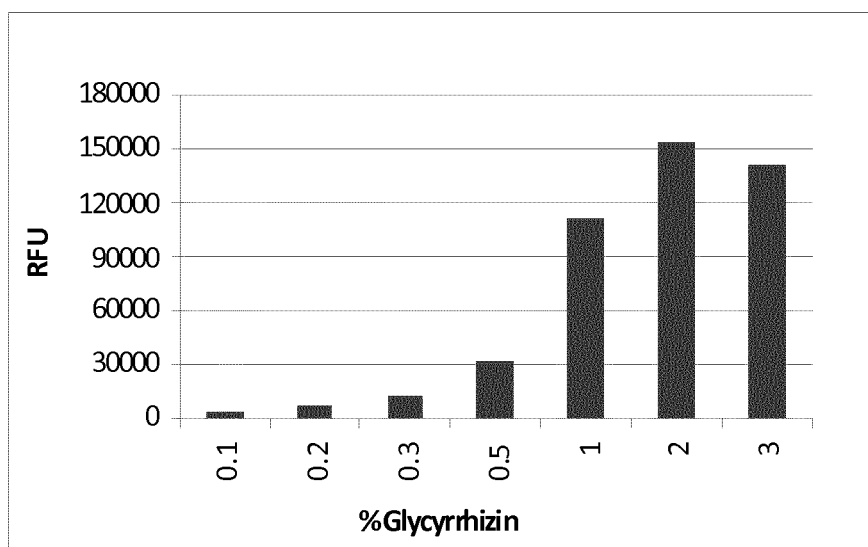
Figure 12:
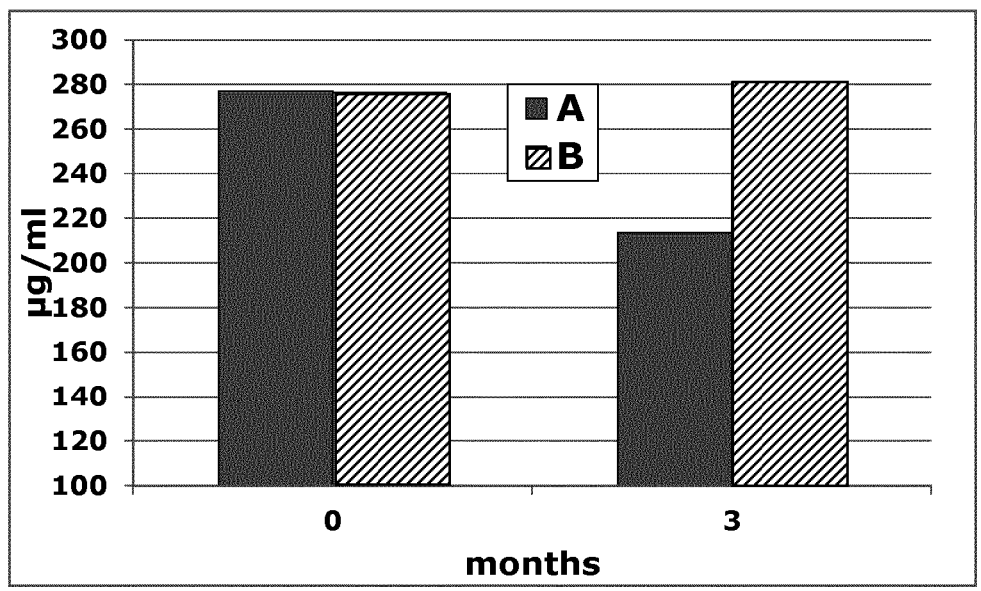
FIG. 12 represents a stability study on dissolved FK-506; 300 µg/ml FK-506 were dissolved in a formulation containing escin and either no dexpanthenol (A) or 60 mg/ml dexpanthenol (B) and stored at 4 degrees C. for 3 months.

The results obtained from the solubility enhancement experiments are described below and are depicted in FIG. 10. The experimental solutions disclosed in Example 3 can be adjusted as pharmaceutical compositions for topical use, particularly for percutaneous or transmucosal administration. In an embodiment, the solutions are adapted as eye drops.

Example 4: Solubility Enhancement of Different Drugs

McIlvaine Buffer containing escin as the saponin component:

1 g escin was weighed and dissolved in a small volume of McIlvaine buffer (buffer composition: 22.52 g $Na_2HPO_4 \times 2$ $H_2O$, 7.73 g citric acid monohydrate, and 4.0 g EDTA dissolved in 1 L of distilled water; pH 6.0), filled up to 250 ml with McIlvaine buffer, and sterile filtered to make a stock solution containing 0.4% (w/v) escin. This escin stock solution was used to prepare samples containing a final concentration of 0.1% escin, herein below referred to as "McIlvaine 0.1%".

Sample Compound Solutions

To prepare 1 ml solutions of the experimental compounds in a buffered solvent containing 10% propylene glycol, 0.1% escin, and 5% dexpanthenol the following compounds were provided in a small container:

250 µl "McIlvaine 0.1%" were mixed with 50 µl dexpanthenol stock solution, brought to 900 µl with distilled water, and combined and vigorously mixed with 100 µl experimental compound pre-dissolved resp. pre-suspended in propylene glycol. Alternative solutions with compound pre-dilutions/pre-suspensions in DMSO were prepared. Samples were centrifuged for 10 min at 15800 rcf. Aliquots of the clear supernatants were transferred into autosampler glass vials and the content of the dissolved experimental compounds was analyzed by HPLC using isocratic elution with 70% or 80% acetonitrile 0.01% TFA/10% or 30% water 0.01% TFA at 1 ml/min and 50° C. for 10 min on an Agilent Zorbax Eclipse Plus C18 column (3.5 µm, 4.6×150 mm) and UV absorbance detection at the wavelengths appropriate for the respective experimental compound.

TABLE 2

Saturation concentrations of stock solutions in different buffers

| Compound | Saturation concentration in 10% propylene glycol or DMSO without escin or dexpanthenol | Saturation concentration in 10% propylene glycol or DMSO, 0.1% escin and 5% dexpanthenol |
|---|---|---|
| Cyclosporine A | 43 µg/ml | 394 µg/ml |
| Tacrolimus/FK506 | 132 µg/ml | 774 µg/ml |
| Lumefantrine | 0.12 µg/ml | 6 µg/ml |
| Lumefantrine (pre-dilution in dimethylsulfoxide) | <0.05 µg/ml | 14 µg/ml |
| Budesonide | 197 µg/ml | 847 µg/ml |
| Fluticasone propionate | 0.68 µg/ml | 5 µg/ml |
| Curcumin | <0.2 µg/ml | 126 µg/ml* |
|  |  | 285 µg/ml** |
| Pimecrolimus | <0.1 µg/ml | 34.5 µg/ml*** |
| Paclitaxel | 2.71 µg/ml | 32.7 µg/ml |

*0.03% escin;
**2% glycyrrhizin instead of escin;
***1% glycyrrhizin instead of escin Example 5 (Comparative Example): Solubility of Budesonide in Aqueous Solution in the Absence of a Saponin Component FIG. 1 represents the solubility of the glucocorticoid budesonide in 0.25× McIlvaine buffer (adjusted to pH 6.0) containing 0%, 5%, 10% and 15% (weight per volume) propylene glycol, without the addition of a saponin component and in the absence of dexpanthenol.

A . . . Buffer
B . . . 5% propylene glycol
C . . . 10% propylene glycol
D . . . 15% propylene glycol
y-axis . . . concentration of dissolved budesonide Even at a propylene glycol concentration of 15 wt %, which is pharmacologically inacceptable for most applications other than topical applications to the skin, the dissolved budesonide concentration is as low as 175 μg/ml.

Example 6: Solubility of Budesonide in Aqueous Solution in the Presence of a Saponin Component FIGS. 2a and 2b refer to the concentrations of budesonide still dissolved after one month of storage at ambient temperature (T~20-25° C.) in 0.25× McIlvaine buffer containing 5% (FIG. 2a) and 10% (FIG. 2b) propylene glycol (maximum concentration 550 μg/ml budesonide). Results indicate that the addition of only 0.01-0.02% w/v of escin dramatically increases the solubility of the steroid. Further increase of escin concentration remains substantially without additional benefit. Adding dexpanthenol as an additional component does not interfere with steroid solubility.

Figure 2A:
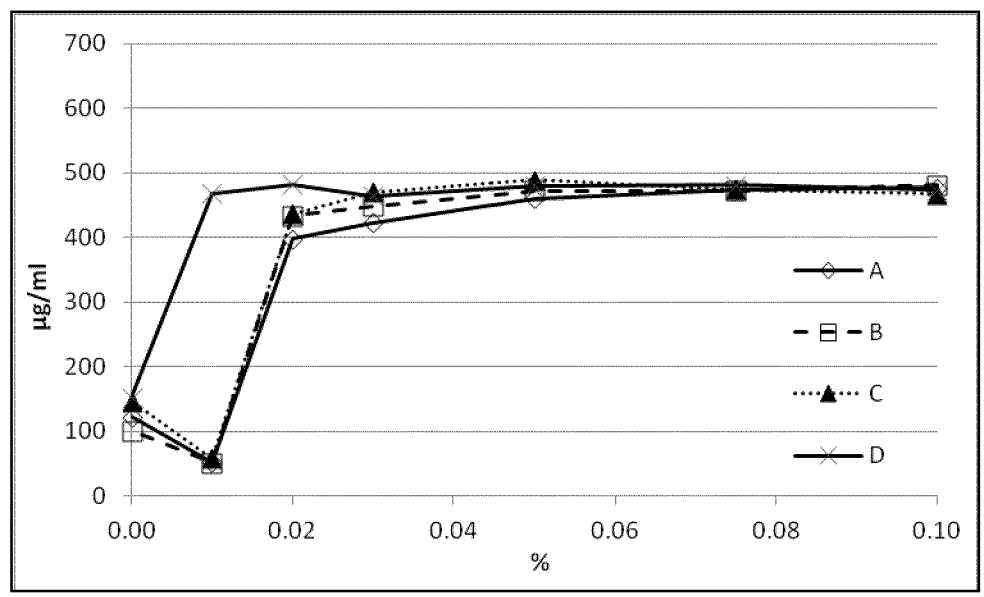
FIGS. 2a and 2b refer to the concentrations of budesonide still dissolved after one month of storage at ambient temperature (T~20-25° C.) in 0.25× McIlvaine buffer containing 5% (FIG. 2a) and 10% (FIG. 2b) propylene glycol (maximum concentration 550 µg/ml budesonide).
Figure 2B:
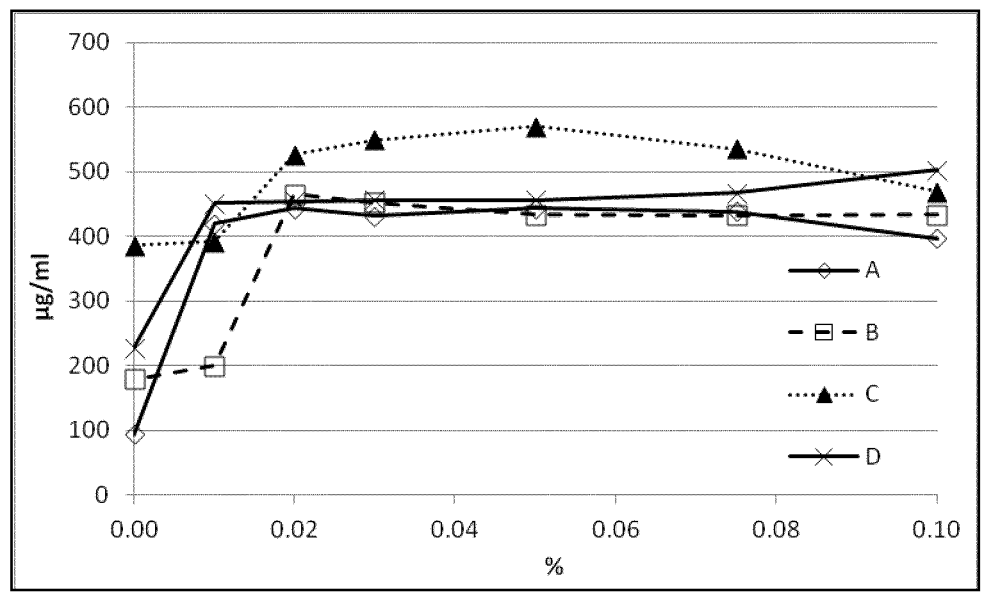

FIG. 2a: 5% propylene glycol; FIG. 2b: 10% propylene glycol
A . . . 0% Dexpanthenol
B . . . 1% Dexpanthenol
C . . . 2% Dexpanthenol
D . . . 5% Dexpanthenol
y-axis . . . μg/ml dissolved budesonide
x-axis . . . w/v % Escin

Example 7: Effect of Dexpanthenol on Storage Stability

Figure 3A:
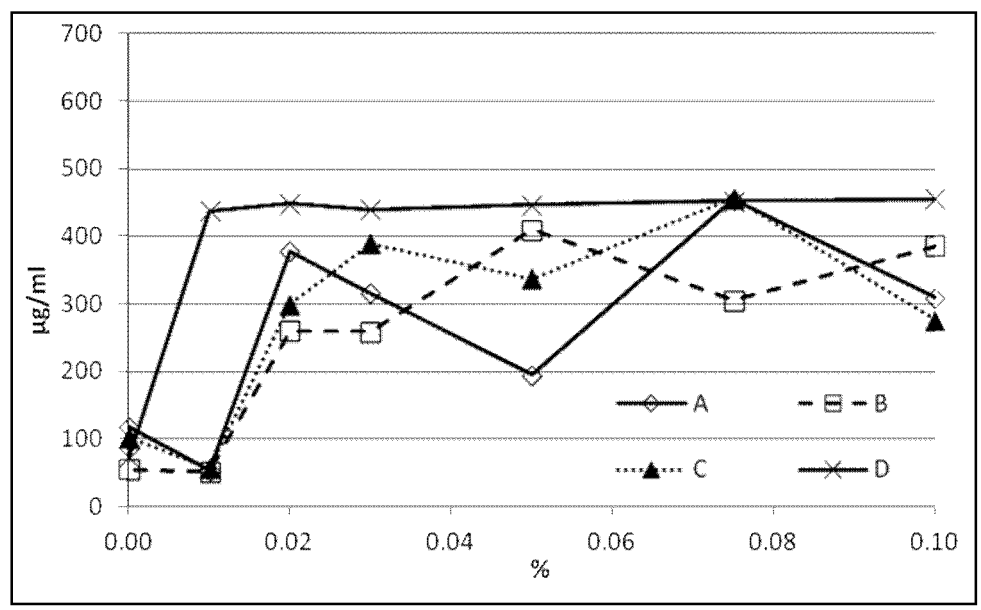
FIGS. 3a and 3b are based on data sets identical to those of FIG. 2a/2b but after 3 months of storage at ambient temperature (T~20-25° C.).
Figure 3B:
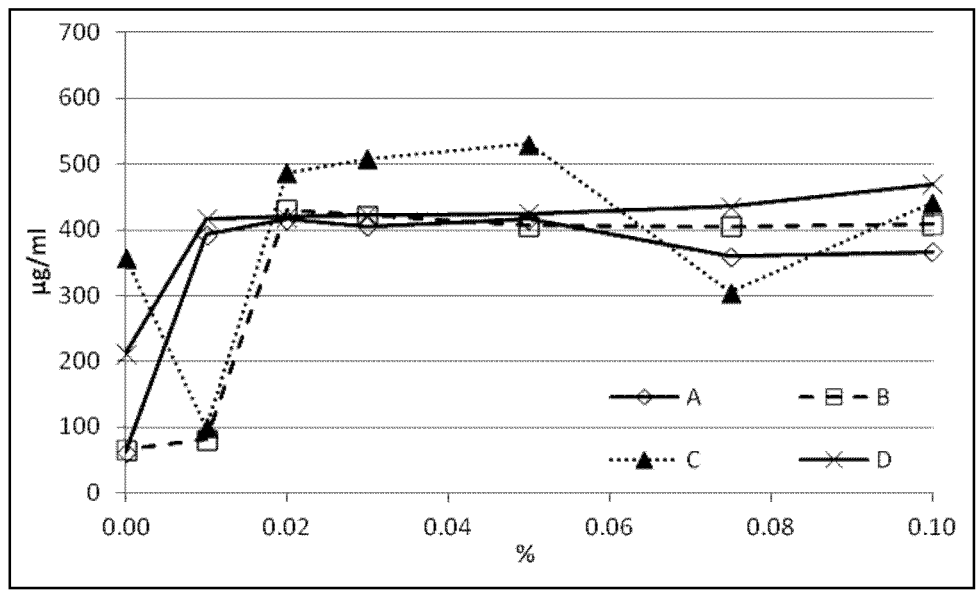

FIGS. 3a and 3b are based on data sets identical to those of FIG. 2a/2b but after 3 months of storage at ambient temperature (T~20-25° C.).

FIG. 3a: 5% propylene glycol; FIG. 3b: 10% propylene glycol
A . . . 0% Dexpanthenol
B . . . 1% Dexpanthenol
C . . . 2% Dexpanthenol
D . . . 5% Dexpanthenol
y-axis . . . μg/ml dissolved budesonide
x-axis . . . w/v % Escin The addition of dexpanthenol seems to improve the stability of the experimental solutions, particularly at lower propylene glycol concentrations (FIG. 3a) and at very low escin concentrations. Also, at 10% propylene glycol in the experimental solution the addition of 2-5% (v/v) dexpanthenol seems to increase the steroid solubility in the absence of escin (FIG. 3b). It may be mentioned at this occasion that the experimental compositions referred to in this example may be advantageously formulated as eye drops.

Example 8: Effect of Dexpanthenol on Budesonide Solubility

Figure 4:
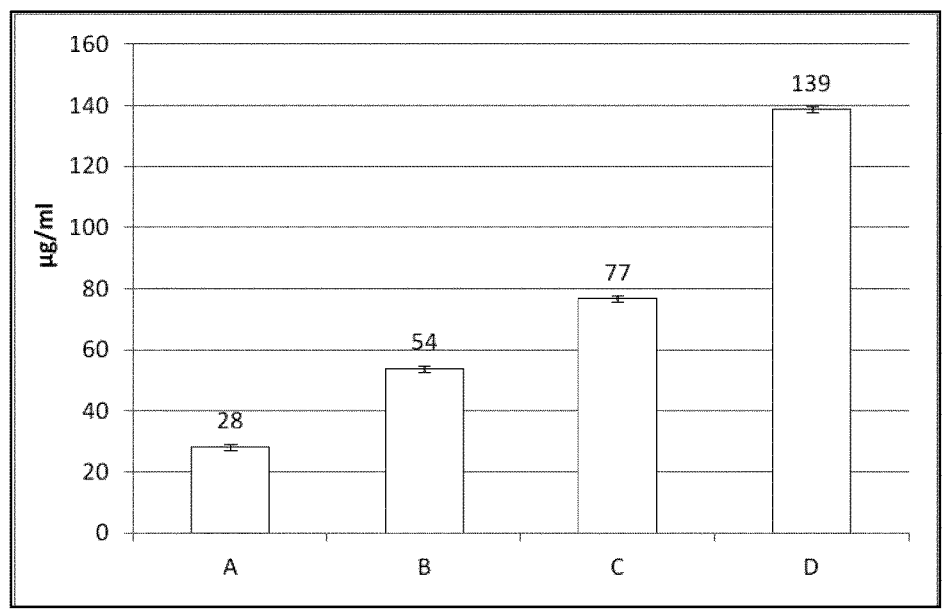
FIG. 4 represents that 0.03% w/v escin and 5% v/v dexpanthenol independently increase the solubility of budesonide in McIlvaine buffer in the absence of propylene glycol.

FIG. 4 represents that 0.03% w/v escin and 5% v/v dexpanthenol independently increase the solubility of budesonide in McIlvaine buffer in the absence of propylene glycol. At 0.03% escin and 5% dexpanthenol (see FIG. 4, col. D) synergy seems to occur, i.e., steroid solubility seems to be augmented beyond a mere additive effect. Yet, the solubility of budesonide in this buffer system, i.e., in the absence of propylene glycol, remains at or below the corresponding values achieved in the presence of propylene glycol alone, i.e., in the absence of escin and dexpanthenol (see FIGS. 2a, b and 3a, b). The only exception being the value at column D which moderately exceeds the solubility values achieved with propylene glycol alone.

A . . . 0% Escin/0% Dexpanthenol
B . . . 0% Escin/5% Dexpanthenol
C . . . 0.03% Escin/0% Dexpanthenol
D . . . 0.03% Escin/5% Dexpanthenol
y-axis . . . concentration of dissolved budesonide in [μg/ml]

Figure 5:
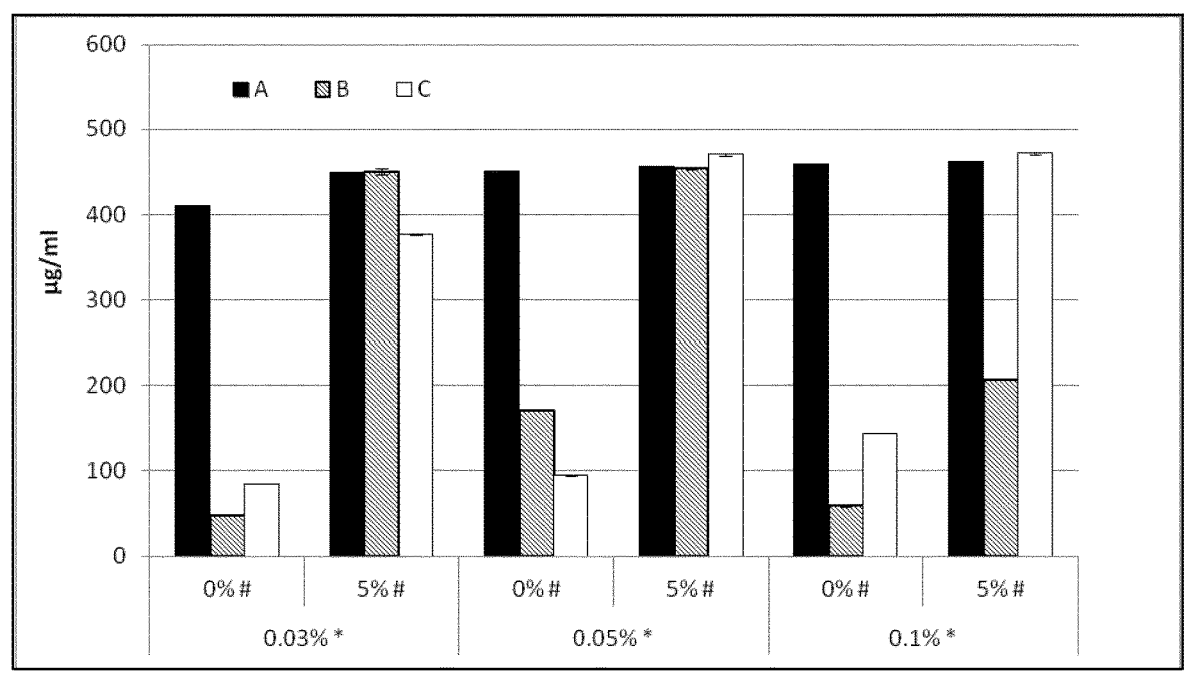
FIG. 5 represents that glycyrrhizin and saponins from Quillaja saponaria extract remain without substantial effect on steroid solubility in the absence of dexpanthenol.

Example 9: Effects of Glycyrrhizin and *Quillaja saponaria* Extract on Steroid Solubility FIG. 5 represents that glycyrrhizin and saponins from *Quillaja saponaria* extract remain without substantial effect on steroid solubility in the absence of dexpanthenol. However, in the presence of dexpanthenol these saponins when provided at concentrations of 0.03% or 0.05%, respectively, in the experimental solutions, are able to improve the solubility of budesonide to an extent comparable to the one achieved with escin at the same concentrations in the absence or presence of 5% dexpanthenol. For *Quillaja* saponins, but not for glycyrrhizin, this applies also at a saponin concentration of 0.1%. Escin exhibits the most consistent performance across all saponin and dexpanthenol concentrations, achieving an up to tenfold increase in budesonide solubility.

A . . . Escin
B . . . Glycyrrhizin
C . . . *Quillaja* extract
* . . . w/v % Saponin component (escin, glycyrrhizin or *Quillaja* ext.)
. . . v/v % Dexpanthenol
y-axis . . . concentration of dissolved budesonide

Example 10: Solubility of Fluticasone Propionate in Various Settings

Figure 6:
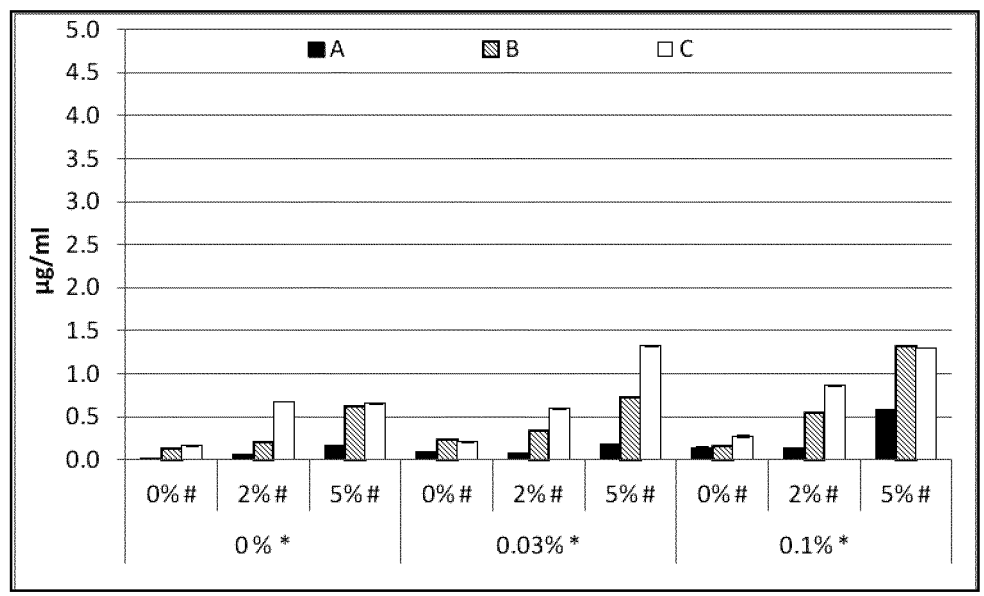
FIG. 6 represents solubility data for the glucocorticoid fluticasone propionate in 0.25× McIlvaine buffer (adjusted to pH 6) containing combinations of propylene glycol (0%, 5%, and 10%), escin (0%, 0.03%, 0.1%) and dexpanthenol (0%, 2%, 5%).

FIG. 6 represents solubility data for the glucocorticoid fluticasone propionate in 0.25× McIlvaine buffer (adjusted to pH 6) containing combinations of propylene glycol (0%, 5%, and 10%), escin (0%, 0.03%, 0.1%) and dexpanthenol (0%, 2%, 5%).

A . . . 0% Propylene glycol
B . . . 5% Propylene glycol
C . . . 10% Propylene glycol
* . . . w/v % Escin
. . . v/v % Dexpanthenol
y-axis . . . concentration of dissolved fluticasone propionate It appears that the best dissolution of the experimental compound is achieved at the highest propylene glycol and dexpanthenol concentrations in the presence of at least 0.03% of the saponin component. It is further derivable from the data that the solubility of fluticasone propionate increases independently with increasing PG concentrations as well as with increasing dexpanthenol concentrations, even absent any saponin component. However, without saponin the best achieved concentration is only about 50% of the maximum concentration obtained in the presence of at least 0.03% saponin, i.e. escin in this example.

Figure 7:
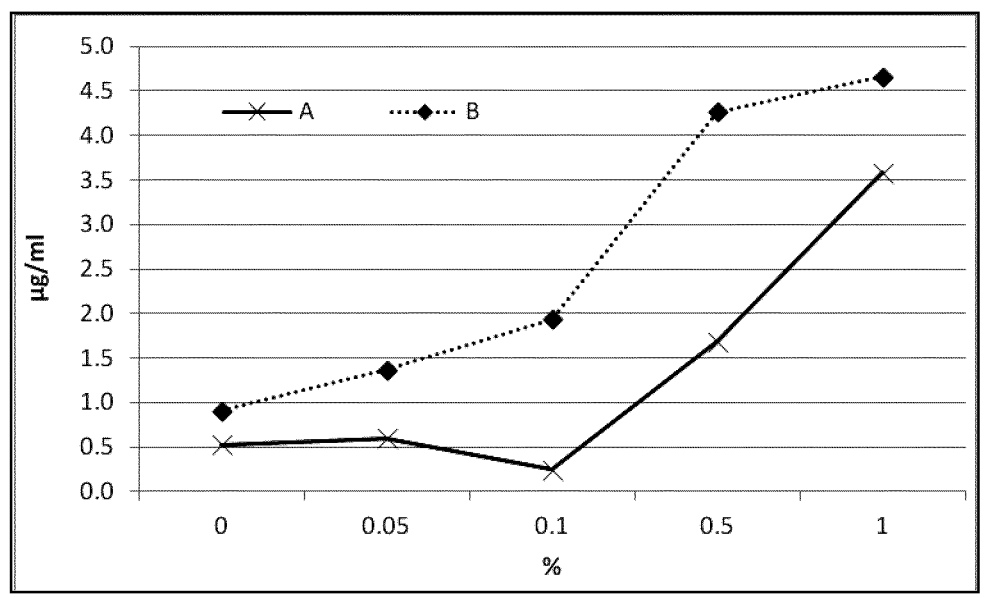
FIG. 7 represents the impact of dexpanthenol and saponin concentration on the dissolution of fluticasone propionate in 0.25× McIlvaine buffer containing 5% propylene glycol (maximum concentration achieved=5 µg/ml). A . . . 0% Dexpanthenol; B . . . 5% Dexpanthenol; x-axis . . . % Glycyrrhizin

Example 11: Effect of Dexpanthenol and Glycyrrhizin Concentrations on the Solubility of Fluticasone Propionate FIG. 7 represents the impact of dexpanthenol and saponin concentration on the dissolution of fluticasone propionate in 0.25× McIlvaine buffer containing 5% propylene glycol (maximum concentration achieved=5 μg/ml). Results demonstrate that an additional content of 0.5-1% glycyrrhizin as a saponin component increases solubility up to ninefold. The presence of 5% dexpanthenol seems to deliver solubility boosting effects.

A . . . 0% Dexpanthenol
B . . . 5% Dexpanthenol
y-axis . . . concentration of dissolved fluticasone propionate
x-axis . . . % Glycyrrhizin

Example 12: Budesonide Solubility in the Presence of a Carrageenan Component FIG. 8a represents the relationship between dissolved budesonide (y-axis) in McIlvaine buffer containing 5% propylene glycol and 1.2 g/L iota-carrageenan, and varying dexpanthenol and escin concentrations after 3 months of storage at ambient temperature (T≈20-25° C.): dexpanthenol concentrations at 0% (series A), 2% (series B), or 5% v/v (series C); x-axis=escin concentrations. FIG. 8b represents analogous data obtained from an identical experimental set up as in FIG. 8a except for the fact that the experimental solution further contained 0.4 g/L kappa-carrageenan.

A . . . 0% Dexpanthenol
B . . . 2% Dexpanthenol
C . . . 5% Dexpanthenol
x-axis . . . w/v % Escin
y-axis . . . µg/ml Budesonide It appears that the highest drug concentrations observed after 3 months storage come with the preparations comprising at least 0.03% escin, as well as with preparations comprising at least 0.02% escin together with the highest tested dexpanthenol concentration, i.e. 5% dexpanthenol. The experimental compositions used in this example and in example 13 hereinafter may advantageously be adapted for use as a nasal spray.

Example 13: Budesonide Solubility and Storage Stability in the Presence of Carrageenan FIG. 9a represents the relationship between the concentrations of dissolved budesonide (y-axis) in McIlvaine buffer containing 10% propylene glycol, 1.2 g/L iota-carrageenan, and optionally dexpanthenol on one hand, and the saponin concentration on the other hand, after one month of storage at ambient temperature; x-axis=escin concentration.

FIG. 9b represents analogous data obtained from an identical experimental set up as in FIG. 9a except for the fact that the experimental solution further contained 0.4 g/L kappa-carrageenan.

A . . . 0% Dexpanthenol
B . . . 2% Dexpanthenol
C . . . 5% Dexpanthenol
x-axis . . . w/v % Escin
y-axis . . . µg/ml Budesonide From the results depicted in FIGS. 8 and 9, it can be inferred that the presence of carrageenans in the experimental solutions do not substantially interfere with the solubility of the experimental steroid compound. At lower propylene glycol concentrations (e.g., 5%), it might be useful to slightly increase the saponin component from 0.01 to 0.02 or 0.03%.

Example 14: Effect of Varying Escin and Dexpanthenol Concentrations on Fluticasone Solubility in the Presence of Hyaluronic Acid FIG. 10 represents the concentrations of dissolved fluticasone propionate (y-axis) in McIlvaine buffer containing 5% propylene glycol, 7.5 g/l hyaluronic acid, and optionally dexpanthenol, in relation to varying escin concentrations (x-axis) after one month of storage at ambient temperature.

A . . . 0% Dexpanthenol
B . . . 2% Dexpanthenol
C . . . 5% Dexpanthenol
x-axis . . . w/v % Escin
y-axis . . . μg/ml Fluticasone propionate Dexpanthenol seems to synergistically boost the solubility enhancing activity of escin on fluticasone propionate under the given circumstances, i.e. in the presence of hyaluronic acid. Absent the saponin component an addition of dexpanthenol at the tested concentrations does not exert any significant effect on fluticasone solubility.

Example 15: Solubilization Correlates with the Presence of Micelles

In water and aqueous buffers containing a detergent below the critical micelle concentration fluorescence of the Hoechst 33342 dye is almost undetectable. Upon increase of the detergent concentration until the critical micelle concentration is reached micelles begin to form and the dye starts getting incorporated into the micelles, whereupon an increase of a fluorescence signal can be detected. For the experiments of this example, the dye was mixed at a final concentration of 7 μM with aqueous buffer comprising different concentrations of saponin in black, flat and clear bottom 96-well plates and emission spectra were measured using a microplate reader (filters used: ex=355 nm and em=460 nm). Finally, data were background corrected.

As shown in FIGS. 11*a* and 11*b* the fluorescence of the Hoechst 33342 dye increases with increasing concentration of saponin. For escin a concentration of 0.02% is sufficient to trigger the formation of micelles. To achieve the same fluorescence level (RFU=relative fluorescent units) with glycyrrhizin a mini-mum concentration of 0.5% (i.e. 25-fold increase) is required. The experiments conducted so far provide clear evidence that micelles are being formed at the saponin concentrations needed for substantially taking the various hydrophobic compounds into solution. Most likely, micelle formation is key to improving the solubilization of such sparingly soluble compounds.

In addition, integrating the hydrophobic organic compounds into micelle structures will also contribute to protecting such compounds from undesired hydrolysis and in case of drugs will assist in maintaining physiological activity.

It is therefore preferred that the method of solubilization carried out in accordance with the present invention is performed in a way that results in the formation of micelle structures in the final preparation. Micelle formation is also envisaged when using glycyrrhizin as a saponin component, as opposed to some state of the art literature teaching the formation of special glycyrrhizin-drug complexes. Accordingly, it is advantageous to dissolve—in a first step—the insoluble or slightly soluble hydrophobic organic compound in a suitable, pharmaceutically or cosmetically acceptable organic solvent at a high concentration and insert this solution—in a second step—into a likewise acceptable aqueous solvent system comprising a saponin component, and optionally dexpanthenol, usually under gentle stirring at a temperature of between 20 and 80 degrees C., particularly between 30 and 40 degrees C., and at a pH of from 4 to 8. Switching the steps of admixture of organic and aqueous solutions to insert the aqueous phase into the organic phase would substantially hamper the formation of micelle structures and thus substantially reduce the advantageous effects of the invention, and is therefore not preferred.

Temperatures above 50 deg C. tend to destroy the micelle structures, and at temperatures of or above 80 deg C. no micelles will be formed, even though temporary overheating may not always be detrimental to the end product, at least where the experimental compound is not heat sensitive. Experiments have shown that subsequent cooling down of shortly overheated preparations to a temperature below 50 deg C. will in most cases restore at least the micelle structures.

Applying pH values outside the preferred range of from pH 4 to 8 will generate undesired side effects, e.g. itching, pain and others, upon administration of the pharmaceutical compositions to mucosal surfaces of e.g. the nose, the eyes, the respiratory tract, the lungs, or the genital and anorectal areas. Also, at pH values below 4 escin tends to decompose while glycyrrhizin tends to solidify. Moreover, pH values above 8 are inacceptable for preparations that are intended for various envisaged kinds of injection including, for example, subcutaneous, intracutaneous, intradermal, intravenous, intramuscular, intraarticular, intrathekal, intraspinal, intracardial, intraperitoneal or intrapulmonal injections.

It is also envisaged herein that the fluorescence dye might be used as an analytical tool for confirming the dissolution of a hydrophobic organic compound in a micelle forming solvent system. It could be applied in a fast and simple method of determining the eligibility of a water insoluble or slightly soluble hydrophobic organic compound for improvement of its solubility in an aqueous solvent system, i.e. wherein detectable fluorescence indicates at least qualitatively if not quantitatively the onset of micelle formation, hence solubilization of the respective compound. It could thus provide guidance for determining the metes and bounds of the present invention by way of a functional rather than structural definition of the compounds eligible for improved solubilization in accordance with the methods of the present invention.

Example 16: Lyophilization Enables Dry Formulations which can be Reconstituted without Substantial Losses Lyophilisation experiments were conducted with dissolved FK-506 containing ethanol as a solvent and trehalose as a lyophilisation enhancer. More specifically, FK-506 dissolved in 100% ethanol was diluted 1:20 to a final solution comprising 5% ethanol, citrate buffer pH 6.0, 1% (10 mg/ml) glycyrrhizin, 0.03% (0.3 mg/ml) escin and 150 mM trehalose. The liquid formulations were deep-frozen in liquid nitrogen and then lyophilised in an Alpha 1-4 LSCplus freeze-drying system. After lyophilisation the formulations were reconstituted in water containing 50 mg/ml dexpanthenol and either 30 mg/ml or 50 mg/ml propylene glycol. The concentrations of dissolved FK-506 prior to lyophilisation and 24 hours after reconstitution were determined by HPLC.

Figure 13:
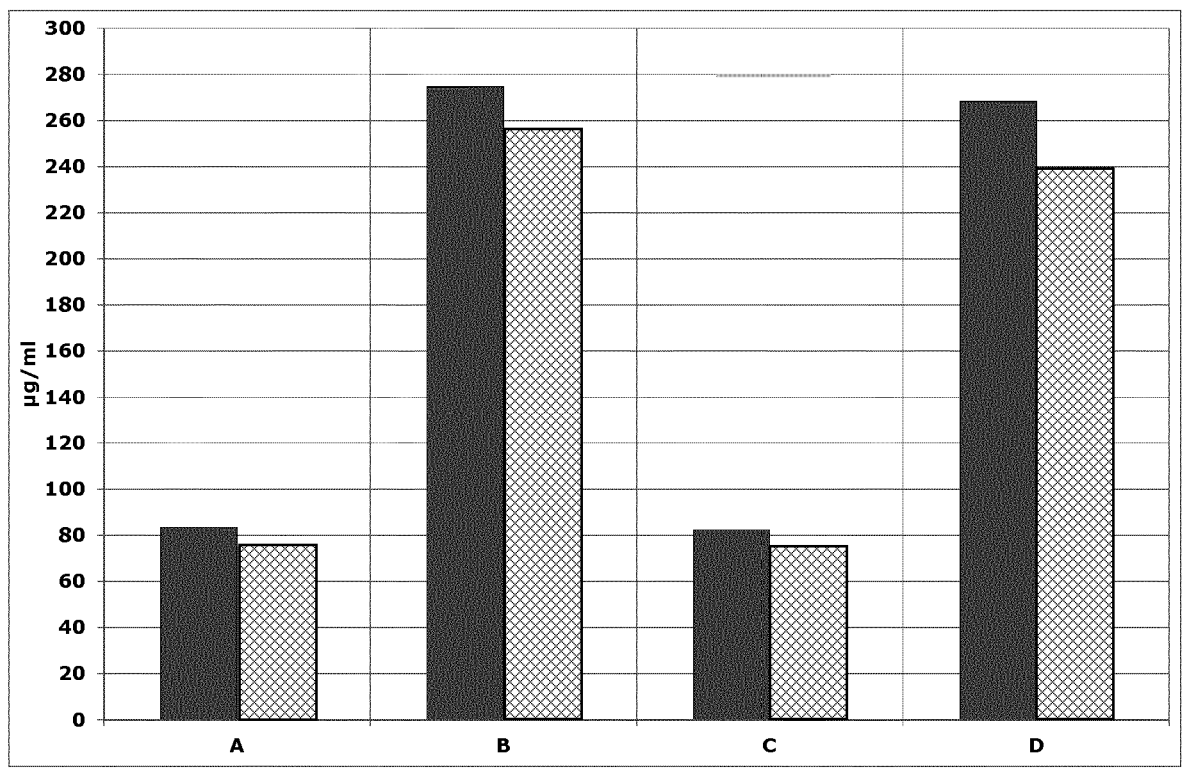
FIG. 13 represents the results of lyophilisation experiments with dissolved FK-506 at two different concentrations, i.e. 100 µg/ml (A, C) and 300 µg/ml (B, D); left, dark columns represent the concentration of dissolved FK-506 prior to lyophilisation; right columns represent FK-506 concentrations 24 hours after reconstitution in water supplemented with 50 mg/ml dexpanthenol and either 30 mg/ml (A, B) or 50 mg/ml (C, D) propylene glycol; y-axis shows µg/ml dissolved FK-506.

In FIG. 13 the upper case letters refer to:
A . . . FK-506 (100 µg/ml); reconstituted at 30 mg/ml (3%) propylene glycol
B . . . FK-506 (300 µg/ml); reconstituted at 30 mg/ml (3%) propylene glycol
C . . . FK-506 (100 µg/ml); reconstituted at 50 mg/ml (5%) propylene glycol
D . . . FK-506 (300 µg/ml); reconstituted at 50 mg/ml (5%) propylene glycol 1 . . . FK-506 before lyophilisation; 2 . . . FK-506 after lyophilisation and reconstitution; y-axis shows µg/ml dissolved FK-506.

As can be derived from FIG. 13 the principle of the present invention can also be applied to produce in a first step a liquid composition of the compound of interest solubilized in accordance with the present invention, and to lyophilize said composition in a second step. Whereupon in a third step reconstitution of the lyophilized material into a cosmetically or pharmaceutically acceptable aqueous composition may be carried out without substantial losses of the respective compound. This means that the compound of interest need not necessarily be stored in its final liquid, cream, gel or ointment etc. form but instead may be stored as a lyophilisate and be reconstituted into the final form using a suitable aqueous buffer system optionally supplemented with dexpanthenol, plus further additives if desired. This may be particularly beneficial for long-term storage of short-lived, readily decomposable, or otherwise quickly deteriorating active substances, among which many useful hydrophobic drugs.

Example 17: Mucosal Administration—Bioavailability Testing

In order to test for the bioavailability of compositions prepared in accordance with the present invention, experiments were conducted ex vivo wherein an experimental composition comprising fluticasone propionate as a compound of interest was compared to a composition comprising the same compound at the same concentration but without a saponin as a solubilization enhancer.

Figure 14:
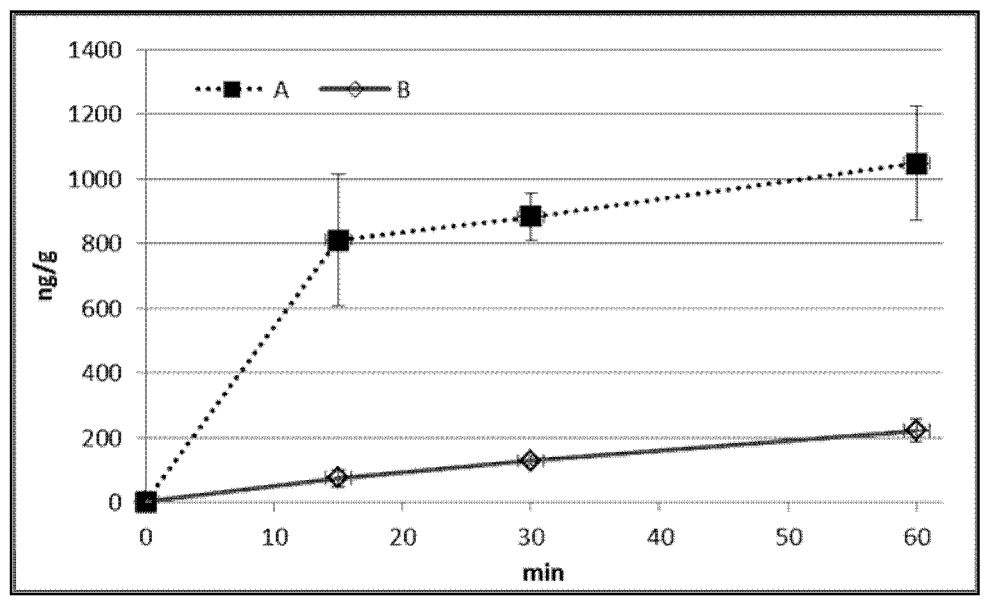
FIG. 14 represents penetration kinetics of fluticasone propionate ex-vivo on porcine nasal mucosa; A (upper line) 5 µg/ml fluticasone propionate prepared according to the invention; B (lower line) 5 µg/ml prepared as a comparative suspension without saponin; x-axis=incubation time in minutes; y-axis=ng fluticasone propionate/g tissue.

FIG. 14 represents the concentrations of fluticasone propionate penetrated ex-vivo into porcine nasal mucosa at different time points. The experimental composition comprised 5 µg/ml fluticasone propionate dissolved in aqueous buffer comprising 0.03% escin, 3% propylene glycol and 5% dexpanthenol. The comparative specimen was a suspension comprising the same aqueous buffer and no saponin nor dexpanthenol. Both formulations were added ex-vivo onto surgically extracted porcine nasal mucosa. After 15, 30, 45 and 60 minutes of incubation the mucosa was washed and the amount of permeated fluticasone propionate was determined by HPLC-MS/MS.
A—experimental composition;
B—comparative fluticasone propionate suspension;
x-axis=incubation time in minutes;
y-axis=ng fluticasone propionate/g tissue.

The results very nicely show that the concentration of active drug that successfully permeated into the mucosal tissue is around five times higher when using the experimental composition prepared in line with the invention as compared to the non-experimental drug suspension.

Example 18: Comparison of In Vivo Physiological Activity of Budesonide

Experiments were conducted in a mouse model to compare bioavailability and physiological activity of budesonide administered by way of state-of-the-art suspension at two different concentrations, as opposed to an experimental composition comprising 0.03% escin, 5% dexpanthenol and 5% propylene glycol in an aqueous buffer.

In an LPS-induced acute lung inflammation model, anesthetized mice were intra-nasally treated 3 hours before LPS challenge either with placebo, or with an experimental solution comprising 300 µg/ml budesonide dissolved, or with comparative compositions of budesonide formulated as dispersions at concentrations of 300 μg/ml and of 1.28 mg/ml, respectively. The LPS induced TNF-alpha release into the bronchoalveolar lavage (BAL) was evaluated 2 hours post challenge as a surrogate parameter for inflammation with a commercially available ELISA-kit. The results are depicted in FIG. 15.

Figure 15:
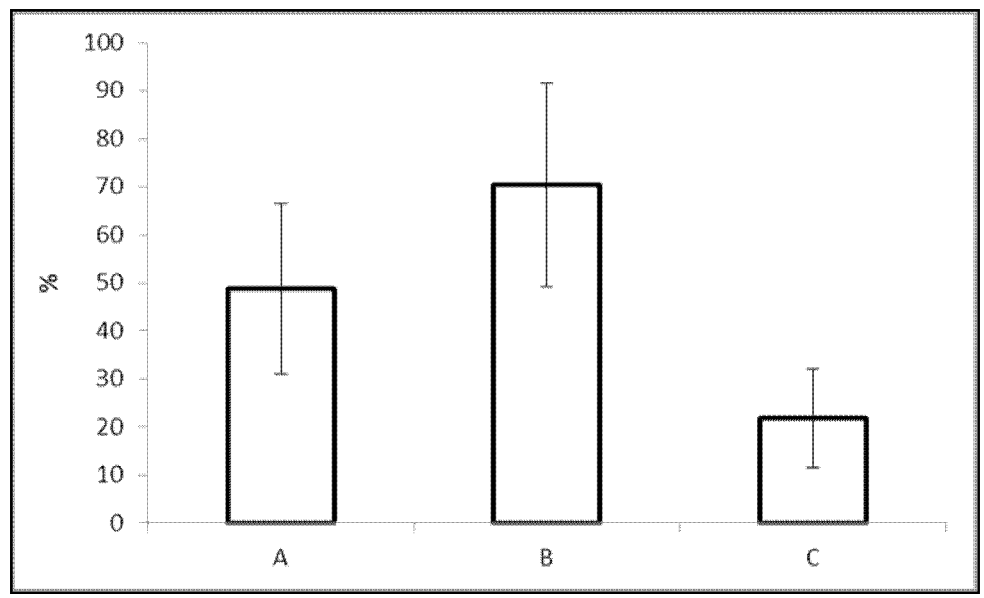
FIG. 15 represents TNF-alpha levels in percent of untreated control (100%) upon administration of budesonide in an LPS-induced acute lung inflammation model; A=comparative budesonide suspension at 1.28 mg/ml.

FIG. 15 represents the respective TNF-alpha concentrations released into the BAL, in percent of a placebo control (=100%).

A—Budesonide suspension (1.28 mg/ml),
B—budesonide suspension (300 μg/ml);
C—budesonide dissolved in experimental solvent (300 μg/ml);
x-axis=samples tested;
y-axis=TNF-alpha released into BAL in % of placebo control (100%).

It can be derived from FIG. 15 that in the in vivo mouse model comparative budesonide formulations are far less effective in depressing TNF alpha levels upon LPS challenge, even at the highest tested concentrations, as compared to the experimental budesonide preparation provided in line with the invention.

It can be inferred from the data obtained from the experiments disclosed in the Examples 1-18 above and represented in the corresponding Figures that the addition of a saponin component such as escin, and optionally dexpanthenol, can increase and optionally stabilize the concentration of a dissolved insoluble or slightly soluble hydrophobic organic compound of interest in an aqueous solvent system up to one or more orders of magnitude. Yet, it shall be emphasized at this occasion that for providing compositions suitable for mucosal or transmucosal applications the maximum concentration of escin should preferably not exceed 0.5% w/v, the maximum concentration of glycyrrhizin should preferably not exceed 5% w/v, the maximum concentration of dexpanthenol should preferably not exceed 5%, and the maximum concentration of propylene glycol should preferably not exceed 10% w/v, of the final ready-for-use composition.

In addition, the experimental results disclosed herein provide clear evidence that escin as a most suitable saponin component not only substantially increases the solubility of several classes of hydrophobic organic compounds but also allows for the conclusion that for a given compound selected from one of these classes it is possible to specifically adjust the concentrations of escin and dexpanthenol in order to achieve the best improvement in solubility and the best stabilization of the resulting solution for long-term storage. Also it can be derived from the data that a successful outcome as described herein does not depend on the presence of any particular chemical structure in the organic compound to be solubilized, as long as it is hydrophobic in nature and water-insoluble or only slightly soluble.

A person of ordinary skill in the art will understand from the present disclosure including the figures referred to herein that the principle of the invention can be applied to improve the solubilization of any hydrophobic organic compound that is insoluble or only slightly soluble in water or aqueous solvents, regardless of whether it is a pharmaceutically active drug, a desired cosmetic ingredient or another chemical substance.

Compounds of particular interest in connection with the present invention comprise various drugs the optimal use of which is frequently hindered due to solubility constraints. The present invention may not only offer an improvement in taking many of them into solution at substantially increased levels but in addition may even expand their utilities into novel fields of medical therapy or cosmetic applicability, as the case may be.

Examples of compounds of interest not yet mentioned hereinbefore of which a poor aqueous solubility could be improved using the present invention comprise inter alia:

a. Analgesics and antirheumatics
such as, e.g., morphine, codeine, piritramide, fentanyl, levomethadone, tramadol, diclofenac, ibuprofen, indomethacin, naproxen, piroxicam;

b. Antiallergics
such as, e.g., pheniramine, dimethindene, terfenadine, astemizole, loratidine, doxylamine and meclozine;

c. Antibiotics and chemotherapeutics
such as, e.g., rifampicin, ethambutol, thiacetazone;

d. Antiepileptics
such as, e.g., carbamazepine, clonazepam, mesuximide, phenytoin, valproic acid;

e. Antimycotics
such as, e.g., natamycin, amphotericin B, miconazole, clotrimazole, econazole, fenticonazole, bifonazole, ketoconazole, tolnaftate;

f. Antimalarials
such as, e.g., chloroquine, mefloquine, artemisinin, primaquine, lumefantrine, halofantrine;

g. Corticoids
such as, e.g., aldosterone, budesonide, fludrocortisone, betamethasone, dexamethasone, triamcinolone, fluocortolone, flucticasone propionate, hydroxycortisone, prednisolone, prednylidene, cloprednol, methylprednisolone h. Dermatics
such as, e.g., antibiotics from the group comprising tetracycline, erythromycin, framycetin, tyrothricin, fusidic acid; virostatics such as vidarabine;
corticoids from the group comprising amcinonide, fluprednidene, alclometasone, clobetasol, diflorasone, halcinonide, fluocinolone, clocortolone, flumethasone, diflucortolone, fludroxycortide, halomethasone, desoximetasone, fluocinolide, fluocortin butyl, fluprednidene, prednicarbate, desonide;

i. Hypnotics and sedatives
such as, e.g., cyclobarbital, pentobarbital, methaqualone, benzodiazepines from the group comprising flurazepam, midazolam, nitrazepam, lormetazepam, flunitrazepam, triazolam, brotizolam, temazepam, loprazolam;

j. Immunotherapeutics and cytokines
such as, e.g., azathioprine, cyclosporin, pimecrolimus, sirolimus, tacrolimus, rapamycin;

k. Local anaesthetics
such as butanilicaine, mepivacaine, bupivacaine, etidocaine, lidocaine, articaine,
oxybuprocaine, tetracaine, benzocaine;

l. Anti-migraine agents
such as, e.g., lisuride, methysergide, dihydroergotamine, ergotamine;

m. Anaesthetics
such as, e.g., methohexital, propofol, etomidate, ketamine, thiopental, droperidol, fentanyl;

n. Parathyroid hormones, calcium metabolism regulators
such as, e.g., dihydrotachysterol o. Ophthalmics
such as, e.g., cyclodrin, cyclopentolate, homatropine, tropicamide, pholedrine, edoxudine, aciclovir, acetazolamide, diclofenamide, carteolol, timolol, metipranolol, betaxolol, pindolol, bupranolol, levobununol, carbachol;

p. Psychotropics such as, e.g., benzodiazepines including lorazepam and diazepam, clomethiazole;

q. Sex hormones and their inhibitors such as, e.g., anabolics, androgens, antiandrogens, gestagens, estrogens, antiestrogens;

r. Cytostatics and metastasis inhibitors such as, e.g., alkylating agents from the group comprising melphalan, carmustine, lomustine, cyclophosphamide, ifosfamide, trofosfamide, chlorambucil, busulphan, prednimustine, thiotepa; antimetabolites from the group comprising fluorouracil, methotrexate, mercaptopurine, tioguanine; alkaloids from the group comprising vinblastine, vincristine, vindesine; antibiotics such as dactinomycin; taxol and related or analogous compounds; dacarbazine, oestramustine, etoposide.

While the experiments disclosed herein have mainly been carried out using escin as the saponin component, it shall be reiterated that also glycyrrhizin and *Quillaja saponaria* extract have been found to exert solubility boosting activities, particularly in the presence of dexpanthenol, as disclosed hereinabove.

What is claimed is:

1. The pharmaceutical or cosmetic composition comprising a water-insoluble or slightly water-insoluble hydrophobic organic compound dissolved in an aqueous solvent system, wherein
    the water-insoluble or slightly water-soluble hydrophobic organic compound is selected from the group consisting of budesonide, tacrolimus and fluticasone;
    the aqueous solvent system comprises:
        a saponin component comprising escin at or above a critical micelle escin at or above a c concentration, wherein the concentration of escin in the aqueous solvent system is in a range of from 0.01% to 0.1% w/v;
        a McIlvaine buffer having a pH of 6;
        propylene glycol at a concentration of from 5-10%; and
        dexpanthenol at a concentration of from 1% to 5%; and
    at least part of the water-insoluble or slightly water-insoluble hydrophobic organic compound is dissolved through solubilization by way of attachment to micelles present in the aqueous solvent system.

2. The pharmaceutical or cosmetic composition of claim 1, wherein the pharmaceutical or cosmetic composition comprises at least one further ingredient selected from the group consisting of iota-carrageenan, kappa-carrageenan, and hyaluronic acid.

3. The pharmaceutical or cosmetic composition of claim 1, wherein the pharmaceutical or cosmetic composition is formulated as a gel, a cream, an ointment, a spray, a mouthwash, a gargling solution, a solution for inhalation, or a suppository, for administration to a mucosal surface.

4. The pharmaceutical or cosmetic composition of claim 3, wherein the mucosal surface is selected from the group consisting of a mucosal surface of the nose, the mouth, the eyes, the respiratory tract, the lungs, the genital region, and the anorectal region.

5. A pharmaceutical or cosmetic composition comprising a water-insoluble or slightly water-soluble hydrophobic organic compound dissolved in an aqueous solvent system, wherein
    the aqueous solvent system comprises a buffer adjusted to a pH value in a range of from pH 4 to pH 8, and a saponin component comprising escin at or above a critical micelle concentration;
    the concentration of escin is in a range of from 0.01% to 0.5% w/v;
    the aqueous solvent system further comprises dexpanthenol at a concentration of from 0.5% to 5% v/v, and a pharmaceutically or cosmetically acceptable non-aqueous organic solvent;
    at least a part of the water-insoluble or slightly water-soluble hydrophobic organic compound is dissolved through solubilization by way of attachment to micelles present in the aqueous solvent system; and
    the water-insoluble or slightly water-soluble hydrophobic organic compound is selected from the group consisting of analgesics, antirheumatics, antiallergics, antibiotics, chemotherapeutics, antiepileptics, antimycotics, chloroquine, mefloquine, artemisinin, primaquine, lumefantrine, halofantrine, curcumin, corticoids, dermatics, hypnotics, sedatives, immunotherapeutics, cyclosporin, tacrolimus, sirolimus, rapamycin, umirolimus, zotarolimus, everolimus, myolimus, novolimus, pimecrolimus, ridaforolimus, temsirolimus, cytokines, anaesthetics, anti-migraine drugs, parathyroid hormones, calcium metabolism regulators, ophthalmics, psychotropics, sex hormones, inhibitors of sex hormones, cytostatics, and metastasis inhibitors.

6. The pharmaceutical or cosmetic composition of claim 5, wherein the pharmaceutically or cosmetically acceptable non-aqueous organic solvent comprises propylene glycol.

7. The pharmaceutical or cosmetic composition of claim 5, wherein the pharmaceutically or cosmetically acceptable non-aqueous organic solvent comprises propylene glycol present in the composition at a concentration of from 1% to 15% v/v.

8. The pharmaceutical or cosmetic composition of claim 5, wherein the pharmaceutically or cosmetically acceptable non-aqueous organic solvent is selected from the group consisting of DMSO, propylene glycol, polyethylene glycols, propylene carbonate, dimethyl isosorbide, fatty acid alcohols, triacetin monostearate, ethylene glycol distearate, glyceryl monostearate, propylene glycol monostearate, polyvinyl alcohol, carbomers, non-ionic polyethoxylated detergents derived from hydrogenated castor oil, and chemically modified cellulose derivatives.

9. The pharmaceutical or cosmetic composition of claim 5, wherein the pharmaceutical or cosmetic composition comprises at least one further ingredient selected from the group consisting of iota-carrageenan, kappa-carrageenan, and hyaluronic acid.

10. The pharmaceutical or cosmetic composition of claim 5, wherein the water-insoluble or slightly water-soluble hydrophobic organic compound is selected from the group consisting of morphine, codeine, piritramide, fentanyl, levomethadone, tramadol, diclofenac, ibuprofen, indomethacin, naproxen, piroxicam, pheniramine, dimethindene, terfenadine, astemizole, loratidine, doxylamine, meclizine, rifampicin, ethambutol, thiacetazone, carbamazepine, clonazepam, mesuximide, phenytoin, valproic acid, natamycin, amphotericin B, miconazole, clotrimazole, econazole, fenticonazole, bifonazole, ketoconazole, tolnaftate, aldosterone, budesonide, fludrocortisone, betamethasone, dexamethasone, triamcinolone, fluocortolone, flucticasone propionate, hydroxycortisone, prednisolone, prednylidene, cloprednol, methylprednisolone, tetracycline, erythromycin, framycetin, tyrothricin, fusidic acid, vidarabine, amcinonide, fluprednidene, alclometasone, clobetasol, diflorasone, halcinonide, fluocinolone, clocortolone, flumethasone, diflucortolone, fludroxycortide, halomethasone, desoximetasone, fluocinolide, fluocortin butyl, prednicarbate, desonide, cyclobarbital, pentobarbital, methaqualone, flurazepam, midazolam, nitrazepam, lormetazepam, flunitrazepam, triazolam, brotizolam, temazepam, loprazolam, azathioprine, butanilicaine, mepivacaine, bupivacaine, etidocaine, lidocaine, articaine, oxybuprocaine, tetracaine, benzocaine, lisuride, methysergide, dihydroergotamine, ergotamine, methohexital, propofol, etomidate, ketamine, thiopental, droperidol, dihydrotachysterol, cyclodrin, cyclopentolate, homatropine, tropicamide, pholedrine, edoxudine, aciclovir, acetazolamide, diclofenamide, carteolol, timolol, metipranolol, betaxolol, pindolol, bupranolol, levobununol, carbachol, lorazepam, diazepam, clomethiazole, anabolics, androgens, antiandrogens, gestagens, estrogens, antiestrogens, melphalan, carmustine, lomustine, cyclophosphamide, ifosfamide, trofosfamide, chlorambucil, busulphan, prednimustine, thiotepa, fluorouracil, methotrexate, mercaptopurine, tioguanine, vinblastine, vincristine, vindesine, dactinomycin, taxol, dacarbazine, oestramustine, and etoposide.

11. The pharmaceutical or cosmetic composition of claim 5, wherein the pharmaceutical or cosmetic composition is formulated as a gel, a cream, an ointment, a spray, a mouthwash, a gargling solution, a solution for inhalation, or a suppository, for administration to a mucosal surface.

12. The pharmaceutical or cosmetic composition of claim 11, wherein the mucosal surface is selected from the group consisting of a mucosal surface of the nose, the mouth, the eyes, the respiratory tract, the lungs, the genital region, and the anorectal region.

\* \* \* \* \*

UNITED STATES PATENT AND TRADEMARK OFFICE
CERTIFICATE OF CORRECTION

PATENT NO. : 11,510,859 B2  
APPLICATION NO. : 15/767290  
DATED : November 29, 2022  
INVENTOR(S) : Andreas Grassauer et al.

Page 1 of 1

It is certified that error appears in the above-identified patent and that said Letters Patent is hereby corrected as shown below:

In the Claims

Claim 1, Column 25, Line 27, replace "The pharmaceutical" with ---Pharmaceutical---.

Claim 1, Column 25, Line 28, after "slightly", replace "water-insoluble" with ---water-soluble---.

Claim 1, Column 25, Line 36, after "micelle", delete "escin at or above a c".

Claim 1, Column 25, Line 43, after "slightly", replace "water-insoluble" with ---water-soluble---.

Signed and Sealed this  
Twenty-fourth Day of January, 2023

Katherine Kelly Vidal  
*Director of the United States Patent and Trademark Office*